US008349328B2

(12) United States Patent
Cayley et al.

(10) Patent No.: US 8,349,328 B2
(45) Date of Patent: Jan. 8, 2013

(54) RODENT CONTROL AGENTS COMPRISING ANTIBODIES THAT BINDS TO RODENT SPECIFIC PEPTIDE EPITOPES

(75) Inventors: Patricia Jane Cayley, Bracknell (GB); Andrew John Dinsmore, Knutsford (GB); Fergus Gerard Paul Earley, Bracknell (GB); Claire Judith Anne Sadler, Holmes Chapel (GB); Jason Leigh Vincent, Bracknell (GB)

(73) Assignee: Syngenta Crop Protection LLC, Greensboro, NC (US)

( * ) Notice: Subject to any disclaimer, the term of this patent is extended or adjusted under 35 U.S.C. 154(b) by 878 days.

(21) Appl. No.: 11/908,347

(22) PCT Filed: Feb. 17, 2006

(86) PCT No.: PCT/GB2006/000562

§ 371 (c)(1),
(2), (4) Date: Jul. 18, 2008

(87) PCT Pub. No.: WO2006/095128

PCT Pub. Date: Sep. 14, 2006

(65) Prior Publication Data

US 2010/0158892 A1 Jun. 24, 2010

(30) Foreign Application Priority Data

Mar. 11, 2005 (GB) .................................. 0505054.7
Jan. 13, 2006 (GB) .................................. 0600719.9

(51) Int. Cl.
*C07K 16/00* (2006.01)

(52) U.S. Cl. ............... 424/139.1; 424/133.1; 424/135.1; 424/152.1; 424/179.1; 530/387.3; 530/387.9; 530/391.7

(58) Field of Classification Search ........................ None
See application file for complete search history.

(56) References Cited

U.S. PATENT DOCUMENTS

| | | | | |
|---|---|---|---|---|
| 4,310,536 | A * | 1/1982 | Boschetti et al. | 514/457 |
| 5,237,051 | A * | 8/1993 | Garbers et al. | 530/350 |
| 5,759,808 | A * | 6/1998 | Casterman et al. | 435/69.1 |
| 6,326,467 | B1 | 12/2001 | Nett et al. | |
| 6,492,498 | B1 * | 12/2002 | Vallera et al. | 530/391.7 |
| 7,371,849 | B2 * | 5/2008 | Honda et al. | 536/24.33 |
| 2005/0009188 | A1 | 1/2005 | Kitto et al. | |

FOREIGN PATENT DOCUMENTS

WO 9722364 6/1997

(Continued)

OTHER PUBLICATIONS

Diaz et al., Immunogenetics. Oct. 2002;54(7):501-12.*

(Continued)

*Primary Examiner* — Michael Szperka
(74) *Attorney, Agent, or Firm* — Brian D. McAlhaney

(57) ABSTRACT

The present invention relates to novel rodent control agents comprising antibodies, or antigen-binding fragments thereof, that bind to proteins expressed in rodents and in particular antibodies or antigen-binding fragments that bind to proteins expressed in the gastrointestinal (GI) tract of rodents, as well as to methods of making such novel rodent control agents. The invention further extends to novel antibodies and antigen-binding fragments for use in rodent control as well as to methods of controlling rodents through the use of such antibodies, antigen binding fragments and novel rodent control agents.

18 Claims, 1 Drawing Sheet

FOREIGN PATENT DOCUMENTS

| | | | |
|---|---|---|---|
| WO | 0158955 | | 8/2001 |
| WO | WO 0158955 | A1 * | 8/2001 |
| WO | WO 03025020 | A1 * | 3/2003 |

OTHER PUBLICATIONS

Portolano et al., J Immunol. Feb. 1, 1993;150(3):880-7.*

Rudikoff et al., Proc Natl Acad Sci U S A. Mar. 1982;79(6):1979-83.*

William E. Paul, M.D., editor, Fundamental Immunology, 3d ed. Raven Press, 1993, p. 242.*

Wikipedia entry for "Rodent", downloaded Dec. 15, 2010.*

Janeway et al., Immunobiology, 3rd edition, 1997, Garland Press Inc., pp. 3:1-3:11.*

Kerrins, et al., "Distribution of resistances to anticoagulant rodenticides in the Norway Rat in England 1995-98;" (2001), pp. 149-159, Proceedings, Advances in Vertebrate Pest Management II, Second European Vertebrate Pest Management Conference, Braunschweig, Germany.

Moore & Wong, 1997, Reproduction, Fertility and Development; 9:125-9.

Smith, et al., 1997, Reproduction, Fertility & Development, 9:85-9.

Saito, et al., "Cloning and characterisation of a rat H+/peptide Cotransporter Mediating Absorption of -Lactam Antibiotics in the Intestine and Kidney," J. Pharmacol Ex. Therapy; vol. 275, pp. 2631-1637 (1995). See entire document, especially Materials and Methods "preparation of antisera" and Figure 2.

Shen, et al., "Localisation of PEPT1 and PEPT2 protin-coupled oligopeptide transporter mRNA and protein in rat kidney;" Am J. Physiol; vol. 276, pp. F658-F665 (1999). See entire document, especially Methods "Preparation of polyclonal antibodies."

Ogihara, et al., "Immuno-localisation of H+/peptide cotransporter in rat digestive tract;" Biochem Biophys Res. Commun; vol. 220, pp. 848-852 (1996). See entire document, especially Materials and Methods and Results.

Miyamoto, et al., "Sequence, tissue distribution and developmental changes in rat intestinal oligopeptide transporter;" Biochim Biophys Acta; vol. 1305, pp. 34-38 (1996). See entire document, especially Figure 2.

Smith, et al., "Species-specificity of a murine immunocontraceptive utilising cytomegalovirus as a gene delivery vector;" Vaccine; vol. 23, pp. 2959-2969 (2005). See entire document.

Wang, et al., "Blocking of pregnancy in mice by immunisation with anti-idiotype directed against monoclonal anti-progesterone antibody;" Proc. Natl Acad Sci USA; vol. 86, pp. 7098-7102 (1989). See entire document, especially Results.

Hannesdottir, et al., "Changes in the reproductive system of male mice immunised with a GnRH-analogue conjugated to mycobacterial hsp70;" Reproduction, vol. 128, pp. 365-371 (2004). See entire documents, especially Results.

Miller, L. A., et al.: "Comparative efficacy of two immunocontraceptive vaccines," Vaccine, Butterworth Scientific, Guildford, GB, vol. 15, No. 17-18, Dec. 1997, pp. 1858-1862, XP004097378; ISSN: 0264-410X, Discussion, Conclusion.

Yoder, C. A., et al.: "Effectiveness of twenty, twenty-five diazacholesterol, avian gonadotropin-releasing hormone, and chicken riboflavin carrier protein for inhibiting reproduction in Coturnix quail." Poultry Science, vol. 83, No. 2, Feb. 2004, pp. 234-44, XP009070730, ISSN: 0032-5791, p. 235, left col., first full paragraph; p. 236, right col., second full paragraph, Discussion: 20, 25 Diazacholesterol.

BE 1 000 534 A5 (Etablissements E. Billen S.P.R.L) Jan. 17, 1989.

Produits Sandoz SA et al: Micro-encapsulation du scilliroside, substance rodenticide (Produits Sandoz SA), Research Disclosure, Mason Publications, Hampshire, GB, vol. 201, No. 20, Jan. 1981, XP007107638, ISSN: 0374-4353.

Nadian A. et al.: "Studies on the development of a microencapsulated delivery system for norbormide, a species-specific acute rodenticide;" International Journal of Pharmaceutics, Amsterdam, NL, vol. 242, No. 1-2, 2002, pp. 63-68, XP002330849, ISSN: 0378-5713.

Eason, Charles T. et al: "Assessment of risks of brodifacoum to non-target birds and mammals in New Zealand," Ecotoxicology, vol. 11, No. 1, Feb. 2002, pp. 35-48, XP002380404; ISSN: 0963-9292.

Gamelin et al: "Rodenticides", EMC—Toxicologie-Pathologie, Elsevier, vol. 2, No. 3, Sep. 2005, pp. 89-97, XP005046051, ISSN: 1762-5858.

* cited by examiner

RODENT CONTROL AGENTS COMPRISING ANTIBODIES THAT BINDS TO RODENT SPECIFIC PEPTIDE EPITOPES

This application is a 371 of International Application No. PCT/GB2006/000562 filed Feb. 17, 2006, which claims priority to GB 0505054.7 filed Mar. 11, 2005, and GB 0600719.9 filed Jan. 13, 2006, the contents of which are incorporated herein by reference.

The present invention relates to novel rodent control agents comprising antibodies, or antigen-binding fragments thereof, that bind to proteins expressed in rodents and in particular antibodies or antigen-binding fragments that bind to proteins expressed in the gastrointestinal (GI) tract of rodents, as well as to methods of making such novel rodent control agents. The invention further extends to novel antibodies and antigen-binding fragments for use in rodent control as well as to methods of controlling rodents through the use of such antibodies, antigen binding fragments and novel rodent control agents.

Rodents have long been recognised as pests and cause a variety of problems. They frequently scavenge their food from that which is destined for human and domesticated animal consumption, thus they cause damage to and contaminate (with urine, faeces & disease) not only growing crops, but also stored food materials. Rodents are also known to be carriers of a wide variety of diseases including for example, Trichinosis, Leptospirosis, Cholera, Bubonic Plague, Typhus, Dysentery, Hantavirus, Salmonellosis, Pasteurellosis, Toxoplasmosis, and Rat bite fever, which may be spread either through direct (e.g. through bites) or indirect (e.g. through dust generated from faeces, urine, and/or saliva, and/or insects which live on or feed off rodents etc.) contact to man and/or other mammalian species. Furthermore, rodents frequently cause physical damage to property, installations and equipment through gnawing and burrowing.

Methods of controlling rodents have thus evolved over the years and these can in general be split into three categories: i) trapping; ii) killing through exposure to chemical agents; and iii) sterilising or reducing the ability of rodents to breed. All three of these methodologies suffer from one or more deficiencies.

For example, mechanical traps that are designed to catch and/or kill rodents are by their nature limited in their use by the number of animals that they can deal with i.e. they may only be able to deal with one animal at a time before they require human intervention to be reset. When one considers the high rate at which rodents can reproduce (with an average litter size of 6-8 and between 10 and 12 litters per year, a single pair of rats can produce as many as 15 000 descendants in a year), it can be seen that trapping is not suitable for large infestations. Furthermore trapping is relatively labour-intensive, requiring regular human intervention and this leads not only to increased cost with pest control but can also frighten away the rodents that are targeted by the traps.

The use of chemical rodenticides is currently the main method for practical rodent control programmes in both urban and agricultural environments. In general chemical rodenticides are either acute or chronic in their action, i.e. the chemical mediates toxicosis either rapidly or slowly after an effective dose has been ingested by the rodent. Acute rodenticides include zinc phosphide, trizinc phosphide, red squill (active ingredient scilliroside), sodium (mono)fluoroacetate, fluoroacetamide, alphachloralose, and thallium sulphate. Some rodenticidal chemicals, such as calciferol, bromethalin and flupropadine, may be described as sub-acute rodenticides in that a lethal dose is ingested in the first 24 hours, but repeated feeding occurs and death is normally delayed for several days, however the distinction between acute and sub-acute acting rodenticides is not always clear. Whilst acute rodenticides are advantageous in that they act very rapidly, they are in general very toxic chemicals and there are safety and environmental concerns associated with their use. Furthermore, survivors of acute poison baiting may become bait-shy, thus reducing the overall efficacy of this method of rodent control.

Chronic rodenticides mediate their effect by acting as anti-coagulants, examples of which include the first generation anticoagulants hydroxycoumarins (e.g. warfarin, coumachlor, coumafuryl, coumatetralyl) and indane-diones (e.g. pindone, diphacinone, chlorphacinone); and the second generation anti-coagulants bromadiolone, brodifacoum, difenacoum, flocoumafen, and difethialone. The use of second generation rodenticides has been widespread over the last 2 to 3 decades, and even longer (3 to 5 decades) for the first generation anti-coagulants. Thus rodent populations have had ample time to develop resistance to this method of control, and resistance/tolerance has been reported to each of the active ingredients mentioned above in various rodent populations and/or species (see Kerrins et al., 2001, "Distribution of resistances to anticoagulant rodenticides in England, 1995-98" pp 149-159 Proceedings, Advances in Vertebrate Pest Management II, Second European Vertebrate Pest Management Conference, Braunschweig, Germany).

A further disadvantage of second-generation anti-coagulants stems from their non-species specific mode of action coupled to their widespread use. For many years there have been concerns over secondary poisoning of predatory and scavenging mammals and birds that consume rodents carrying anti-coagulant residues. Both brodifacoum and flocoumafen have been restricted to indoor use in the United Kingdom as they are thought to pose an unacceptably high risk of secondary poisoning if used outside. However, widespread resistance to the more widely used difenacoum and bromadiolone may encourage misuse of the more potent anti-coagulants the use of which is restricted to indoors. More recently low-levels of residues and a lethal impact of such residues have been observed in a wide range of non-target species that are of considerable conservation importance e.g. Barn Owls, Stoats, Weasels, Polecats and Kestrels.

A third method of rodent control that has been proposed, but which has not as yet achieved any real commercial success, relies on reducing rodent birth rate. The use of reproductive inhibitors, such as contraceptives and gametocides, as well as the use of biological and chemical sterilants have all been investigated. However, each approach suffers from some disadvantage. For example, whilst the use of chemical or steroidal compounds as anti-fertility agents has proved successful for captive animals, they are more-difficult to employ with free-ranging pest populations. The compounds are unpalatable and thus it is difficult to ensure that rodents obtain an adequate dose. The gametocide alphachlorohydrin has been marketed as a toxicant-sterilant, however, it has variable effects in different species and is toxic (leading to up to 50% mortality) at higher doses. More recent research has examined immunocontraception as a method of rodent control (see for example, US Patent Application No 2005/0009188; Moore & Wong 1997, Reproduction Fertility & Development 9:125-9; Smith et al., 1997, Reproduction, Fertility & Development, 9:85-9). However, there are difficulties with efficacy when route of administration is oral, due to problems of oral tolerance, and adjuvants may be required.

There is thus a need for novel rodent control agents (i.e. agents that are capable of controlling a population of rodents, for example through killing rodents or by regulating the ability of a population of rodents to breed), which overcome some of the disadvantages suffered by current methods of rodent control. The present invention addresses this need by providing novel rodent control agents that comprise an antibody component, which binds to an extracellular epitope of a protein that is expressed in rodents (such a protein is referred to herein as a target protein). Thus in a first aspect of the invention there is provided a rodent control agent comprising an antibody component that binds to an extracellular epitope of a protein that is expressed in a rodent.

By targeting the rodent control agent to a specific protein and/or specific tissue in a rodent, for example to a protein expressed in the rodent gut tissue/the rodent GI tract, the length of time that the novel rodent control agent is in contact with rodent gut is increased relative to that of non-specific rodent control agents, which merely pass through the gut and are not retarded through specific binding. This may in turn lead to an effective increase in potency of the novel rodent control agent, thus enabling it to be used at lower concentrations than traditional non-specific rodenticides, such as anticoagulant rodenticides.

Preferably the antibody component confers on the novel rodent control agent selectivity for rodents over non-target animals (e.g. humans, birds, companion animals, farm animals, and wild-animals that are not pests). This selectivity for rodent tissue/rodent protein over non-target species is further advantageous as it is likely to reduce the need for antidotes and has the potential to reduce the environmental impact of the novel rodent control agent on non-target species.

Where the antibody component recognises a target protein that performs a non-essential function in the rodent, it will be necessary for the rodent control agent to further comprise a toxic component or a contraceptive component.

Thus in one embodiment the invention provides a rodent control agent comprising an antibody component linked to either a toxic component or a contraceptive component. Such novel rodent control agents may be in the form of a fusion protein, wherein the toxic component or contraceptive component is a protein or peptide moiety that is linked either directly or indirectly (i.e. via a peptide linker) to the antibody component via a peptide bond, or in the form of a protein conjugate, wherein the toxic or contraceptive component is either a small molecule (i.e. a non-proteinaceous, chemical, entity) or protein or peptide moiety that is directly chemically conjugated to the antibody component.

Where the antibody component recognises a target protein that performs an essential function in the rodent (for example, a protein that performs an essential function in the GI tract of a rodent), the antibody component may achieve the rodent control function as the sole functional agent. Such a rodent control agent would mediate its effect by virtue of the antibody component binding to the essential target protein and thus blocking or inhibiting the function of the essential protein. Thus in a further embodiment the present invention provides a rodent control agent comprising an antibody component that binds to an extracellular epitope of a protein that is expressed in a rodent, wherein the protein performs an essential function in the rodent. Examples of suitable target proteins against which antibody components according to this aspect of the invention bind (and thus which may be used in producing antibody components according to this aspect of the invention) include a rodent Sox10 gene product, a rodent endothelin receptor (EDNRB), a rodent endothelin-3 ligand (EDN3), a rodent CFTR (see Table 1 below and the Examples for more detail), rodent IL-2, rodent IL-10, rodent T-cell receptor alpha and/or beta chains, rodent components of the class II major histocompatibility complex. The skilled man will appreciate that some of the above-mentioned gene products/proteins are not readily accessible on an epithelial surface of a rodent and thus require internalisation before they are capable of mediating their activity. In such a case, it may be desirable to combine an antibody component directed to one of the above proteins with a further targeting antibody component, which enhances the probability of internalisation. Thus two or more antibody components, one directed against one of the afore-mentioned proteins and a second acting as targeting antibody to a suitable epithelial target to enhance internalisation, may be linked, either via conjugation or by virtue of a fusion protein as described hereinafter.

The term "antibody component" is used herein to mean an antibody or antigen-binding fragment thereof, which binds to an extracellular epitope of a protein that is expressed in a rodent. Preferably the epitope to which the antibody component binds has an amino acid sequence that is only found in a rodent protein, i.e. the antibody binds to a rodent specific epitope or RSE. Rodent specific epitopes (RSEs), which may be used in the generation of antibody components for use in rodent control agents of the invention and to which rodent control agent of the invention bind, form a second aspect of the invention described herein. Antibody components which bind to RSEs are considered as a third aspect of the invention described herein.

The RSE will be extracellular to facilitate access of the antibody (or antigen-binding fragment) to its binding site. Preferably the target protein providing the RSE will be expressed in or on an epithelial surface of the rodent including, for example, the epithelia of the nose, mouth, eyes, gastro-intestinal tract, genito-urinary tract and epidermis. Most preferably the protein will be expressed in (or on) the gastro-intestinal epithelium of a rodent.

In one embodiment the RSE will be provided by a continuous (i.e. sequential) peptide sequence (i.e. the first amino acid residue of the epitope will be directly linked via a peptide bond to the second amino acid residue of the epitope, the second amino acid residue of the epitope will be linked via a peptide bond to the third amino acid residue, etc.). Such a continuous peptide epitope is referred to herein as a rodent-specific peptide epitope or RSPE. RSPEs to which antibody components of the invention bind, and which may thus be used in generating antibody components (and also rodent control agents) of the invention, may be determined by comparative bioinformatic analysis of proteins that are expressed in the desired target tissue/cell layer as indicated by literature and database information, followed by confirmatory immunological analysis. RSPEs, like RSEs, are found in nature only in rodent proteins. An RSPE is defined herein as an oligopeptide fragment of a target protein, wherein the oligopeptide sequence represents an extracellular continuous peptide epitope that has a percentage identity of 60% or less with a corresponding linear peptide sequence from a homologous protein from a non-target (i.e. non-rodent, for example, human) animal.

The term "oligopeptide fragment" as used herein refers to a fragment of a target protein, said fragment consisting of at least about 4 and at most about 50 amino acids. Preferably said oligopeptide fragment will be between 9 and 45 (inclusive) amino acids in length and more preferably said oligopeptide fragment will be between 9 to 30 (inclusive) amino acids in length. In specific embodiments said oligopeptide fragment will be 9, 10, 11, 12, 13, 14, 15, 16, 17, 18, 19, 24 or 44 amino acids in length.

Preferably the percentage of identity between the RSPE and the non-target protein will be such that an antibody component of the invention has high specificity and affinity for the RSPE and will not cross-react with a non-rodent protein of the same class/family as that from which the RSPE was derived. In preferred embodiments the percentage identity between the RSPE and the non-target protein, and in particular between the RSPE and a corresponding linear (i.e. continuous or sequential) peptide sequence from a homologous protein from a non-target animal, is less than or equal to 50%, 45%, 40%, 35%, 30%, or 25%.

Preferably RSPEs will be highly conserved between all target rodent species, in particular highly conserved between rats and mice, especially between two or more of *Rattus rattus, Rattus norvegicus* and *Mus musculus/Mus domesticus*. By highly conserved it is meant that the percentage identity between a RSPE from one rodent species and the corresponding RSPE from a second rodent species will be high. Preferably the percentage identity between two rodent RSPEs will be at least 75%. More preferably the percentage identity will be greater than or equal to 80%, 85%, 90% or 95%, 96%, 97%, 98%, or 99%. Most preferably the RSPE will be 100% identical between two or more rodent species.

Although it is preferred that the percentage identity between of an RSPE is highly conserved between two or more species as discussed above, if the desired high level of conservation is not observed, different RPSEs may be used from proteins (either homologous or different) from two or more rodent species, to generate different antibody components, which may then be combined in a rodent control agent as described hereinafter (e.g. each antibody component linked to a toxic/contraceptive component with the rodent control agent thus comprising multiple different antibody-toxin/contraceptive molecules or the rodent control agent comprising a toxic/contraceptive component linked to two or more different antibody components, each of the two or more antibody components recognising an RSPE from a protein from a different rodent species). In one specific embodiment, an antibody component recognising mouse MDR1 (SEQ ID NO: 8–) could be combined with an antibody component recognising rat MDR1 (SEQ ID NO: 9), in rodent control agents of the invention.

Examples of target proteins to which antibody components of the invention bind, and which may be used in producing or identifying antibody components of the invention, are given in Table 1. This Table also provides examples of specific RSPEs which may be derived from the exemplary proteins. The skilled man will appreciate that neither the list of proteins given in Table 1, nor the list of RSPEs derived therefrom, is exhaustive. Further suitable RSPEs may be identified within the given proteins (all of which are expressed in the GI tract), and further proteins, for example from other rodent target tissues such as the nasal epithelia, buccal epithelia, epidermis, epithelia of the genito-urinary tract and epithelia of the eye, may also be used to produce antibody components of the invention.

TABLE 1

Examples of Proteins which may be targeted by antibodies of the present invention, and specific examples of RSPEs which may be derived from such proteins.

| Source Protein | SwissProt/ GenPept Accession Number | RSPE primary amino acid sequence | SEQ ID NO |
|---|---|---|---|
| Rat oligopeptide transporter PepT1 | P51574 | VIRSRASDGCLEVKE | SEQ ID NO: 1 |
| Rat oligopeptide transporter PepT1 | P51574 | CSSDFKSSNLD | SEQ ID NO: 2 |
| Rat CD155 (PVR, Tage4) | Q9R1E1 | SNVNGSYREMKETGSQP | SEQ ID NO: 3 |
| Rat GTR2 (GLUT2) glucose transporter | P12336 | GTDTPLIVTPAHTTP | SEQ ID NO: 4 |
| Rat CFTR chloride transporter | P34158 | LKNNPVNGGNNGTKIA | SEQ ID NO: 5 |
| Rat CNT2 nucleoside transporter | Q62773/ Q9QWI3 | WQDKESSLRNLAK | SEQ ID NO: 6 |
| Rat CATB(0+) (slc6a14) colonic amino acid transporter | XP233305 | GGDMFMNISWVN | SEQ ID NO: 7 |
| Rat CATB(0+) (slc6a14) colonic amino acid transporter | XP233305 | DTGGDMFMNISWVNS | SEQ ID NO: 36 |
| Rat MDR1 multidrug resistance transporter | P43245 | SFTPSRDPHSDRAIT | SEQ ID NO: 8 |
| Mouse MDR1 multidrug resistance transporter | P06795 | SFTKAEASILPSIT | SEQ ID NO: 9 |

TABLE 1-continued

Examples of Proteins which may be targeted by antibodies of the present invention, and specific examples of RSPEs which may be derived from such proteins.

| Source Protein | SwissProt/ GenPept Accession Number | RSPE primary amino acid sequence | SEQ ID NO |
|---|---|---|---|
| Rat Sucrase-Isomaltase | P23739 | YNAESITNENAGLKATL | SEQ ID NO: 10 |
| Mouse GLUT7 glucose transporter | XP487836 | NTPHKVLKSFYN | SEQ ID NO: 11 |
| Mouse GLUT7/Rat GTR5 (GLUT5) glucose transporters | XP487836/ P43427 | YYDRNKENIES | SEQ ID NO: 12 |
| Rat Npt2a (slc34a1) sodium/phosphate transporter | Q06496 | PETKEASTSMSRVEA | SEQ ID NO: 13 |
| Rat OATP-B (SLC21A9) organic anion transporting polypeptide | Q9JHI3 | LGAQPGPSLFPGCSEPCS CQSDDF | SEQ ID NO: 14 |
| Rat OATP-B (SLC21A9) organic anion transporting polypeptide | Q9JHI3 | QPGPSLFPGCSEPCSCQ | SEQ ID NO: 15 |
| Rat ASBT apical sodium-dependent bile transporter | Q62633 | DAEFLEKTDNDMD | SEQ ID NO: 16 |
| Rat CaT1 (ECAC2) calcium transporter | Q9R186 | QAFQQQDDLYSE | SEQ ID NO: 17 |
| Rat OATP3 organic anion transporting polypeptide | O88397/ Q9EQR8 | SYKGVQHQLHVESKVL | SEQ ID NO: 18 |
| Rat ABCG8 sterol transporter | P58428/ Q8CIQ5/ Q923R7 | QIQFNGHIYTTQIG | SEQ ID NO: 19 |
| Rat GTR8 (GLUT8) glucose transporter | Q9JJZ1/ Q9JMA6 | HVGLLVPISAEPADVHLG | SEQ ID NO: 20 |
| Rat MRP1 multidrug resistance associated protein/ABC transporter | Q810E4/ Q8CG09/ Q810G9 | MFAGPEILELIINF | SEQ ID NO: 21 |
| Rat CNT1 sodium-nucleoside cotransporter | Q62674 | HSHSSLPEGEGGLNKA | SEQ ID NO: 22 |
| Rat UT-B urea transporter | P70633/ P97689 | PSKLFMPVSSVP | SEQ ID NO: 23 |
| Rat DRA1 chloride/ anion exchanger | Q924C9 | LSSSSAENDSMIEEKVMV | SEQ ID NO: 24 |
| Mouse ENT1 equilibrative nucleoside transporter | Q9JIM1/ Q99K84/ Q9DBT8/ Q9JHF0 | KARHCGAQRHHFVFKH | SEQ ID NO: 25 |
| Rat ENT1 equilibrative nucleoside transporter | O54698 | TNQSCESTEALADPSVSL | SEQ ID NO: 26 |
| Rat GCC (guanylyl cyclase) | P23897 | VSGRFPSERS | SEQ ID NO: 27 |

TABLE 1-continued

Examples of Proteins which may be targeted by antibodies of the present invention, and specific examples of RSPEs which may be derived from such proteins.

| Source Protein | SwissProt/ GenPept Accession Number | RSPE primary amino acid sequence | SEQ ID NO |
|---|---|---|---|
| Rat PLB (phospholipase B) | O54728 | AEDLWIQAKELVRHLKDNP | SEQ ID NO: 28 |
| Rat LPH (lactase-phlorizin hydrolase) | Q02401/ Q63712/ Q63719 | EDAAPTASPVQS | SEQ ID NO: 29 |
| Mouse LPH (lactase-phlorizin hydrolase) | XP129479 | RYVQVCALCRFSTVFSPRLPEPVKGERRFSHISLNQDLPRPLFP | SEQ ID NO 30 |
| Rat AMPN (aminopeptidase N) | P15684/ Q9JHP4 | GSTSATTSTTNPA | SEQ ID NO: 31 |
| Rat MCDL (mucin and cadherin-like protein) | Q9JIK1 | NKDILLTTVPMETERTIR | SEQ ID NO: 32 |
| Rat SCAB (amiloride-sensitive sodium channel beta-subunit) | P37090/ O09183 | LPQDLVGMGYAPDRI | SEQ ID NO: 33 |
| Rat SCAB (amiloride-sensitive sodium channel beta-subunit) | P37090/ O09183 | SSNPAPGST | SEQ ID NO: 34 |
| Rat KCV2 (potassium voltage-gated channel subfamily V member 2) | XP220024 | DQRHGKGSPREHDLE | SEQ ID NO: 35 |

Examples of preferred target proteins for use in the invention are the rat oligopeptide transporter PepT1, rat CD155, rat GTR2, rat CFTR, rat CNT2, rat CATB(0)+, rat MDR1, mouse MDR1, rat sucrase-isomaltase, mouse GLUT7, rat OATP-B, rat ENT1, rat GCC, rat PLB, rat LPH, rat AMPN, rat MCDL, and rat SCAB.

Preferred RSPEs of the invention have SEQ ID NOs: 1, 2, 3, 4, 5, 6, 7, 8, 9, 10, 15, 26, 27, 28, 29, 31, 32 and 34.

Particularly preferred target proteins for use in the invention are rat oligopeptide transporter PepT1, rat CD155, rat CFTR, rat CNT2, mouse GLUT7, rat GCC, rat PLB and rat LPH.

Particularly preferred RSPEs of the invention have SEQ ID NOs 1, 3, 5, 6, 11, and 27, 28 and 29.

The skilled man will appreciate that antibodies recognise tertiary protein structure and that an epitope may comprise amino acid residues that are distributed throughout the primary amino acid sequence of a protein whilst being structurally in close proximity to each other. Thus in a further embodiment antibody components (and thus also rodent control agents) of the invention may recognise a discontinuous extracellular RSE.

Antibodies for use in the invention may be polyclonal or monoclonal. Such antibodies may be obtained by immunising an animal with a RSPE as described above, or by immunising an animal with the intact rodent target protein. Polyclonal antibodies of the invention may be obtained from the serum of such an immunised animal, see for example, Example 2. Polyclonal antibodies which recognise the RSPE or rodent target protein but which do not recognise a homologous protein from a non-target animal may be identified using standard immunological techniques (for example by ELISA, and/or through immunohistochemistry against appropriate tissue sources).

Monoclonal antibodies for use in the invention may be obtained by isolating B-lymphocytes from the spleen of an animal immunised with an RSPE or rodent target protein and making a hybridoma cell-line with such lymphocytes. The hybridoma cell-lines are then screened for those which secrete antibodies that recognise the RSPE or rodent target protein but which do not recognise a homologous protein from a non-target animal, see for example, the Examples.

Preferred polyclonal and monoclonal, antibodies for use in the invention are described herein in the Examples.

Antibodies and antigen-binding fragments for use in the invention may also be isolated from a bacteriophage display library (naive, or immune) of antibodies or antigen-binding fragments, or from a similar yeast or bacterial display library of antibodies or antigen-binding fragments, or from a ribosomal display library of antibodies or antigen-binding fragments. Typically such display libraries will be screened to identify displayed proteins that bind to RSPEs or rodent target proteins. The skilled man will be familiar with the methodology for screening such libraries, identifying binding-partners in the library and subsequently isolating such members. Antibody and antigen-binding fragment display libraries which may be used for screening, and their construction are described in the art (see for example: International Patent Publication Nos WO 01/90190 & WO 93/19172; U.S. Pat. Nos. 5,759,808 & 6,517,829; review by Hoogenboom 1997, Trends in Biotechnology 15(2):62-70; Dooley et al., 2003 Molecular Immunology 40: 25-33; Nutall et al., 2001 Molecular Immunology 2001, 38:313-326; and Hanes et al., 1998 Proceedings of the National Academy of Sciences USA 95: 14130-14135). Again antibodies or antigen-binding fragments identified in this way will be checked to confirm that they do not bind to a homologous protein from a non-target animal.

Antibodies for use in the invention may be of any immunoglobulin class, e.g. they may be an IgA, IgD, IgE, IgG or IgM antibody. Preferably an antibody of the invention will be an IgG antibody. Antibodies of the invention may be immunoglobulin molecules comprising both heavy and light chains, or they may be single-chain antibodies. The term "single-chain antibody" as used herein encompasses both naturally occurring antibodies which consist of only a single-type of chain e.g. Camelid or Chondricthyes (shark) derived antibodies, which are devoid of light chains, as well as engineered antibodies that consist of only a single polypeptide chain. Examples of such engineered antibodies include for example, single chain antibodies or "minibodies" as described in International Patent Publication No. WO94/09817 and single-chain variable fragments (scFv). Antibodies of the invention are preferably single chain antibodies. In one preferred embodiment the antibody is a scFv. In another preferred embodiment the antibody is a single-chain antibody devoid of light chains, most preferably a Camelid derived antibody (for example as described in International Patent Publication No. WO 94/04678).

Antigen-binding fragments for use in the invention include immunoglobulin light chains, immunoglobulin heavy chains, $V_H$ domains, $V_L$ domains, Fvs, Fabs, di-Fabs, Fab's, F(ab')$_2$s, $V_{HH}$ domains, IgNAR V domains and CDRs. The skilled man will be very familiar with antigen-binding fragments such as immunoglobulin light and heavy chains, $V_H$ and $V_L$ domains, Fvs, Fabs, di-Fabs, Fab's, F(ab')$_2$s, and CDRs, and their preparation. A$V_{HH}$ domain is the variable domain of a Camelid antibody. $V_{HH}$ domains and their isolation are described in the art, see for example International Patent Publication No. WO 94/04678, International Patent Publication No. WO 01/90190 and the references contained therein. IgNAR antibodies are single-chain antibodies from sharks, which, in common with the Camelid antibodies, are devoid of light chains (see Greenberg et al., 1995 Nature 374:168-173). The antigen-binding region of these antibodies, the IgNAR variable domain (IgNAR V domain), has also been described in the art, see for example Dooley et al., 2003 (Molecular Immunology 40:25-33) and references cited therein. In some embodiments, the antibody component for use in the invention will be a Camelid antibody, or a $V_{HH}$ domain, which recognises one of the preferred target proteins described hereinbefore. In particular, Camelid antibodies or $V_{HH}$ domains which bind to any one of SEQ ID NOs 1, 3, 5, 6, 11, or 27 are preferred, whilst $V_{HH}$ domains binding to any one of SEQ ID NOs 5, 6, 11 or 27 are particularly preferred.

Antibodies and antigen-binding fragments used in the invention may also be engineered to increase their stability, for example they may be stabilised by disulfide bridges (see for example Reiter et al., 1996, Nature Biotechnology 14(10): 1239-1245).

As described above, antibody components may be obtained by using intact rodent proteins or RSEs (which term includes RSPEs), either as antigens or to screen for suitable antibodies/antigen-binding fragments, which have been selected as having a low percentage identity to homologous proteins from non-target (i.e. non-rodent, for example, human) animals. The probability of an antibody component of the present invention cross-reacting with a homologous protein from a non-target species is thus reduced. Thus, in preferred embodiments of the invention, antibody components (and thus also rodent control agents of the invention) exhibit selectivity for an epitope on a rodent target protein rather than the corresponding epitope on a homologous protein from a non-target animal. In other words preferred antibody components of the invention show selectivity to a RSE by binding thereto (or to the rodent protein from which the RSE is derived) with a greater affinity than to a corresponding epitope on a homologous protein (or the homologous protein) from a non-target animal. Non-target animals include humans, birds, companion animals, farm animals, and wild-animals that are not pests.

Preferably antibody components of the invention will exhibit reduced binding to, and even more preferably not bind, to homologous proteins from humans. Even more preferably antibody components of the invention will not only exhibit reduced binding (or not bind) to homologous proteins from humans, but will also exhibit reduced binding (or not bind) to homologous proteins from at least one other non-target animal.

For the avoidance of doubt, the term "bind" insofar is used herein to describe the interaction of an antibody component of the invention with an epitope or protein in a qualitative or quantitative manner.

Where the term is used qualitatively, specificity for binding to a target protein, RSE or RSPE may be demonstrated by the ability of the antibody component to bind to the target protein, RSE, or RSPE in a displaceable manner, wherein displacement of antibody binding results from the presence of the antigen to which the antibody component was raised or screened (referred to hereinafter as the "specific antigen"). If binding of such a target-protein/RSE/RSPE-specific antibody component to a non-target protein (or a corresponding epitope from a non-target protein) is not observed, or if some binding to a non-target protein (or corresponding epitope from a non-target protein) is observed which is not displaceable by the specific antigen, then the antibody component will be deemed as showing selectivity for the target protein, RSE or RSPE (as appropriate) in that the antibody component binds to the target protein/RSE/RSPE with a greater affinity than to a non-target protein or corresponding epitope from a non-target protein. Specificity and selectivity may thus be determined through immunohistochemical analysis of appropriate tissue samples, and/or through ELISA with appropriate samples.

Where the term "bind" is used quantitatively, this means that the antibody component has an affinity of at least $10^{-6}$ M for the epitope or protein with which it interacts. Preferably the affinity will be at least $10^{-7}$M, more preferably $10^{-8}$M, more preferably $10^{-9}$M, even more preferably $10^{-10}$M and most preferably $10^{-11}$M or greater. Thus where an antibody component binds to an RSE or RSPE (or the protein from which the RSE or RSPE is derived) it will have an affinity of at least $10^{-6}$M, and in further embodiments it will have an affinity of at least $10^{-7}$M, at least $10^{-8}$M, at least $10^{-9}$M and at least $10^{-10}$M. In preferred embodiments the antibody component will either not bind to a corresponding epitope on a homologous protein from one or more non-target species (preferably human) i.e. the affinity of the antibody component for a homologous protein from a non-target species will be less than $10^{-6}$M, or it will exhibit reduced binding thereto i.e. the affinity of the antibody component for a homologous protein from a non-target species will be at least 10-fold less than for the target rodent protein. Thus, in preferred embodiments, where an antibody component of the invention has an affinity of at least $10^{-6}$M for an RSE or RSPE (or the protein from which the RSE or RSPE is derived), the affinity of the antibody component for a homologous protein from a non-target species will be less than $10^{-6}$M, and preferably $10^{-5}$M or lower; where an antibody component of the invention has an affinity of at least $10^{-7}$M for an RSE or RSPE (or the protein from which the RSE or RSPE is derived), the affinity of the antibody component for a homologous protein from a non-target species will be $10^{-6}$M or lower; where an antibody component of the invention has an affinity of at least $10^{-8}$M for an RSE or RSPE (or the protein from which the RSE or RSPE is derived), the affinity of the antibody component for a homologous protein from a non-target species will be $10^{-7}$M or less, and preferably $10^{-6}$M or lower; where an antibody component of the invention has an affinity of at least $10^{-9}$M for an RSE or RSPE (or the protein from which the RSE or RSPE is derived), the affinity of the antibody component for a homologous protein from a non-target species will be $10^{-8}$M or lower, and preferably $10^{-6}$M or lower.

The affinity of the antibody component to target and non-target proteins (as well as to epitopes therefrom) may be determined using any appropriate technique; for example, through the use of surface plasmon resonance (e.g. with BIAcore™).

In one embodiment of the present invention the rodent control agent is in the form of a fusion protein, wherein the fusion protein comprises a first protein component and a second protein component, said first protein component is an antibody component as described hereinbefore, and said second protein component is selected from the group consisting of a toxin, an immunogen and a hormone.

The first protein component may be linked directly to the second protein component, however, it is preferred that the two components will be indirectly linked through a linker peptide. The linker peptide will in general be of a length that is sufficient for the first component and second components to function as desired without one component adversely effecting the function of the other (for example by steric hindrance). An example of a commonly used linker peptide, suitable for use in this aspect of the invention is the $(Gly_4Ser)_n$ linker, where "n" is an integer greater than or equal to 1. Typically n is greater than or equal to 3. Preferably, the primary sequence of the linker peptide is designed to be stable in harsh hydrolytic and thermal environments. This may be achieved by removing or mutating residues in the linker that act as recognition sites for processing of the linker via, for example, a proteolytic mechanism. Further examples of suitable linker peptides are those described by Gustavsson et al., 2001 (Protein Engineering 14:711-715), Hennecke et al., 1998 (Protein Engineering 11:405-410) and Huston et al., 1991 (Methods in Enzymology 203:46-88).

In a further embodiment, it is desirable to engineer specific instability into the linker peptide such that controlled separation of the two protein components/release of the second protein component is effected upon delivery of the fusion protein to an appropriate locus, e.g. once the fusion protein has been internalised the second protein component may be released intracellularly. The described control of separation may serve to enhance the activity of certain fusion proteins.

As mentioned above, in one embodiment of the fusion protein, the second protein component is a toxin. The toxin confers on the fusion protein a rodenticidal activity: it effects toxicity against a targeted rodent cell via either an externally- or internally-mediated mode-of-action. Suitable toxins for use in this aspect of the invention include inter alia proteins which disrupt membranes, ribosyltransferases, serine proteases, guanylyl cylase activators, proteins involved in ATPase mediated ion transport, calmodulin-dependent adenylyl cyclases, RNA glycosidases and ribonucleases. Specific examples of suitable toxins are given below in Table 2. The skilled man will appreciate some of the toxins listed in Table 2 are representative of a family of toxin molecules and where this is the case, any one of those members may also be used in the invention.

TABLE 2

Examples of proteins which may be used as toxins in fusion proteins of the invention.

| Protein | Mode-of-Action | SwissProt/ UniProt Accession Number | EMBL Accession No |
|---|---|---|---|
| Perfringolysin O (theta toxin) | cholesterol-dependent pore-forming cytolysin | P19995 | M81080 |
| Alpha-haemolysin (Hla) | pore-forming cytolysin | P09616 | X01645 |
| Sphingomyelinase (beta toxin) | phospholipase C/membrane disrupting | P09978 | X61716 |
| Delta-haemolysin | cationic amphipathic pore-forming lytic peptide | P01506 | AF230358 |
| Granzyme B | serine protease/inducer of apoptosis | P04187/ P18291 | X04072/ M34097 |
| Alpha toxin | phospholipase C/membrane disrupting | P15310 | X17300 |
| Cyt toxin e.g. Cyt 2a | pore-forming/membrane disrupting | Q04470 | Z14147 |
| Diphtheria toxin | NAD(+)-diphthamide ADP-ribosyltransferase | P00588 | X00703 |
| Granulysin | pore-forming/membrane disrupting | P22749 | X54101 |
| Melittin | cationic amphipathic pore-forming lytic peptide | P01501 | X02007 |
| Perforin | Calcium-binding pore-forming cytolysin | P14222 | M31951 |
| Cholera enterotoxin | NAD(+) ADP-ribosyltransferase | P01555/ P01556 | X00171 |
| Heat-stable enterotoxin | guanylyl cyclase activator | Q47185 | M18345 |
| Equinatoxin | pore-forming cytolysin | P61914 | U41661 |
| Listeriolysin | cholesterol-dependent pore-forming cytolysin | P13128 | X15127 |

TABLE 2-continued

Examples of proteins which may be used as toxins in fusion proteins of the invention.

| Protein | Mode-of-Action | SwissProt/ UniProt Accession Number | EMBL Accession No |
|---|---|---|---|
| VIP2 | NAD(+) ADP-ribosyltransferase | Q844J9 | AY245547 |
| Accessory enterotoxin | ATPase-mediated ion transport | P38441 | Z22569 |
| Aerolysin | cholesterol-dependent pore-forming cytolysin | P09167 | M16495 |
| BinA/BinB | pore-forming cytolysins | P06575/ P10565 | Y00378/ X07992 |
| Colicin E1 | transmembrane depolarisation | P02978 | J01563 |
| Haemolysin A | pore-forming cytolysin | P08715 | M14107 |
| CTX IV | protein kinase C inhibitor | P01443 | Y12491 |
| Type 2 Ribosome-inactivating proteins, e.g. Ricin | rRNA N-glycosidase | P02879 | X03179 |
| Amoebapore | pore-forming peptide | P34095 | M83945 |
| El Tor haemolysin | pore-forming/membrane-disrupting cytolysin | P09545 | Y00557 |
| *Vibrio damsela* Haemolysin | phospholipase D/membrane disrupting | Q60079 | L16584 |
| Pneumolysin | cholesterol-dependent pore-forming cytolysin | P11990 | X52474 |
| Streptolysin O | cholesterol-dependent pore-forming cytolysin | P21131 | M18638 |
| thermostable direct haemolysin (Kanagawa toxin) | pore-forming cytolysin | P19249 | D90101 |
| Leptospira haemolysin | pore-forming/membrane disrupting | O34095 | U89708 |
| Cry toxin e.g. Cry1Ac | pore-forming cytolysin | P05068 | M11068 |
| Anthrax toxin | proteolytic attack of kinases in target cell/calmodulin-dependent adenylyl cyclase | P15917/ P13423/ P40136 | M29081/ M22589/ M23179 |
| *Pseudomonas* exotoxin A | NAD-dependent ADP-ribosyltransferase | P11439 | K01397 |
| Barnase | ribonuclease | P00648 | M14442 |
| VIP3 | pore-forming cytolysin | Q45792 | L48811 |
| Thionin | Cytolytic plant toxin | P01543 | AF004018 |
| Type 1 Ribosome-inactivating proteins e.g. Gelonin | rRNA N-glycosidase | P33186 | L12243 |
| Beta-purothionin | Cytolytic plant toxin | P01543 | AF004018 |

Preferred toxins for use in embodiments of the invention include granzyme B, cyt 2A, β-purothionin, VIP2A, gelonin, and granulysin. Particularly preferred toxins are selected from the group consisting of granzyme B, cyt2A, β-purothionin, VIP2A and gelonin.

Protein toxins as described above, may be incorporated in their entirety in fusion proteins of invention. Alternatively, where a domain or fragment of such a toxin confers the toxic activity, that domain or fragment may be employed as the second protein component in the fusion protein.

In another embodiment the second protein component in a fusion protein of the invention is an immunogen, i.e. a poly- or oligo-peptide that is capable of eliciting an immune response in rodents. In a preferred embodiment, immunogen-fusion proteins of the invention will be capable of acting as immunocontraceptives and will thus act as rodent control agents by preventing reproduction. Sperm or ovum specific antigens, such as for example, lactate dehydrogenase C, the sperm antigen PH-20 (Primakoff et al., 1988 Nature 335:543-6), fertilin (PH-30) and zona pellucida antigens are thus suitable immunogens for use as the second protein component in fusion proteins of the invention.

In yet another embodiment, the second protein component in a fusion protein of the invention is a hormone or proteinaceous hormone mimetic. In this embodiment, the second protein component will interfere with and prevent reproduction in rodents and the fusion protein thus acts as a rodent control agent through the prevention of breeding. An example of a hormone that may be used in this embodiment of the invention includes gonadotrophin releasing hormone.

In further embodiments, fusion proteins as described above may comprise at least one further protein component. This further protein component (or components) may be a toxin, immunogen, hormone or proteinaceous hormone mimetic as described above. Accordingly a fusion protein may be constructed comprising an antibody component and at least two further protein components, wherein each of the further protein components confers a rodent control (i.e. toxic or contraceptive, or both) function on the fusion protein. The second and further protein component or components may each have the same, or different rodent control functions (i.e. they may each independently be toxic or contraceptive), and where they have the same function they may each have the same, or independently different, mode of action. Where the additional protein component(s) have the same rodent control function and wherein at least one additional protein component has a different mode of action to the second protein component, the efficacy of the rodent control agent may be enhanced (relative to a rodent control agent comprising a single protein component conferring the rodent control activity). For example a fusion protein, wherein the second protein component is a cell-disruptive toxin (e.g. is selected from the group consisting of perfringolysin O, alpha haemolysin, sphingomyelinase, delta-haemolysin, alpha toxin, cyt toxin, granulysin, melittin, perforin, equinatoxin, listeriolysin, aerolysin, haemolysin A, amoebapore, El Tor haemolysin, *Vibrio damsela* haemolysin, pneumolysin, streptolysin O, Kanagawa toxin, *leptospira* haemolysin, cry toxin, VIP3, thionin and β-purothionin) and the further protein component(s) may be a toxin that requires internalisation within a cell for activity (e.g. selected from the group consisting of granzyme B, diphtheria toxin, cholera endotoxin, VIP2, accessory enterotoxin, colicin E1, CTX IV, a type 2 ribosome inactivating protein such as ricin, anthrax toxin, *Pseudomonas* exotoxin A, barnase, a type 1 ribosome inactivating protein such as gelonin), may be a particularly effective rodent control agent as the membrane-disrupting activity conferred by the second protein component may assist the functional activity of the further protein component by facilitating access of the further protein component to the inside of a rodent cell. In preferred embodiments the fusion protein will comprise at least one toxin component selected from the group consisting of: cyt2A, β-purothionin, and granulysin; and at least one toxin component selected from the group consisting of granzyme B, VIP2A, and gelonin.

Fusion proteins of the invention may be constructed so that the first protein component (the antibody component) is N-terminal to the second protein component, alternatively they may be constructed so that the second protein component is N-terminal to the first protein component. As mentioned previously, in some embodiments it is desirable to indirectly link the two protein components via a linker peptide. Thus fusion proteins of the invention may comprise from N to C terminus, the first protein component linked via a peptide bond to a linker peptide, which is in turn linked via a peptide bond to the second protein component, or they may comprise from the N to C terminus the second protein component linked via a peptide bond to a linker peptide, which is in turn linked via a peptide bond to the first protein component.

Where the fusion protein comprises an additional protein component this may be N-terminal to the first component i.e. the additional protein component is linked either directly through its C-terminal residue via a peptide bond to the N-terminal residue of the first protein component, or indirectly via a peptide linker (or a further protein component) to the N-terminal residue of the first protein component. In a further embodiment the additional protein component is N-terminal to the second protein component i.e. the additional protein component is linked either directly through its C-terminal residue via a peptide bond to the N-terminal residue of the second protein component, or indirectly via a peptide linker (or a further protein component) to the N-terminal residue of the second protein component. In still further embodiments the additional protein component may be i) C-terminal to the first component i.e. the additional protein component is linked either directly through its N-terminal residue via a peptide bond to the C-terminal residue of the first protein component, or indirectly via a peptide linker (or a further protein component) to the C-terminal residue of the first protein component; or C-terminal to the second protein component i.e. the additional protein component is linked either directly through its N-terminal residue via a peptide bind to the C-terminal residue of the second protein component, or indirectly via a peptide linker (or a further protein component) to the C-terminal residue of the second protein component.

Antibody components and/or fusion proteins of the invention may be produced by expressing nucleic acids encoding them in any suitable protein expression system. Thus in a further aspect, the invention provides nucleic acids encoding fusion proteins of the invention. Nucleic acids encoding fusion proteins of the invention may obtained by cloning a nucleic acid encoding the first protein component in-frame with a nucleic acid encoding the second protein component. Where the first and second protein components are indirectly linked via a peptide linker, a nucleic acid encoding the linker will separate and be in-frame with the two protein components of the fusion protein.

Nucleic acids encoding antibody components may be isolated using standard molecular biological techniques from hybridoma cells expressing an antibody of the invention. Alternatively, nucleic acids encoding antibody components may be obtained, again using standard molecular biological techniques, from phage display or other library clones that encode an antibody or antigen-binding fragment of the invention.

Nucleic acids sequence encoding examples of the second protein component (the toxic or contraceptive component) are available in the art, see for example the EMBL database references in Table 2.

Nucleic acids encoding linker peptides may be synthesised de novo, for example from oligonucleotides encoding the linker peptide sequence.

In order for an antibody component or fusion protein to be expressed in a suitable protein expression system the nucleic acid encoding the fusion protein will be operably linked to a suitable promoter, and optionally a suitable transcription terminator. In general, the promoter to which the nucleic acid encoding the fusion protein is operably linked will be any promoter capable of driving expression of the fusion protein in the host cell into which the nucleic acid is to be introduced. Thus, if it is desired that the antibody component or fusion protein be expressed in a bacterial cell, the promoter will be operable in that bacterial cell. Similarly if it is desired that the antibody component or fusion protein be expressed in a fungal expression system the promoter will be operable in a fungal cell and the same logic prevails if the construct is to be introduced into a mammalian cell culture expression system or a plant expression system. The use of a seed-specific promoter is particularly desirable when the antibody component or fusion protein is to be expressed in plant cells and/or plants. Where nucleic acids of the invention are operably linked to a suitable transcriptional terminator region, this will be one that mediates the termination of transcription in the host cell in which the antibody component or fusion protein of the invention is to be expressed. Transcriptional terminator regions suitable for this purpose are described in the art.

Suitable expression systems for expression of antibody components and/or fusion proteins of the invention include microbial expression systems such as bacterial (e.g. *E. coli*, *Bacillus* expression systems) and fungal systems e.g. yeasts (such as, for example, *Saccharomyces cerevisiae*, *Schizosaccharomyces pombe*, *Pichia* species, *Hansenula* species), and other fungal expression systems (e.g. filamentous fungal expressions systems derived from *Aspergillus* species, *Trichoderma reesei*, and *Neurospora crassa*); mammalian expression systems e.g. CHO cells, and plant expression systems. Preferred plants and plant cells for use in the expression of fusion proteins of the invention include wheat, barley, maize, sorghum, oats, rice and millet. The skilled man will be familiar with these expression systems, which are described fully in the art.

Novel rodent control agents as described herein may also be in the form of a protein conjugate. Thus, in a further aspect the invention provides a protein conjugate comprising an antibody component of the invention as described herein, chemically conjugated to a toxic component or contraceptive component. In one embodiment the toxic component or contraceptive component will be a small chemical entity, whilst in a further embodiment the toxic component or contraceptive component will be a protein or peptide as described hereinbefore with respect to fusion proteins of the invention. Where the toxic component is a small chemical entity, examples of suitable toxic compounds for use in this aspect of the invention include colchicine; doxorubicin; calicheamicin; molecules of the non-steroidal anti-inflammatory drug (NSAID) class; cytochalasin; anticoagulants such as brodificoum, difenacoum, bromadiolone, flocoumafen, difethialone, hydroxycoumarins, indane-diones; calciferol; bromethalin; flupropadine; zinc phosphide; scilliroside; sodium (mono) fluoroacetate; fluoroacetamide; alphachloralose; thallium sulphate.

Where the contraceptive component is a small chemical entity, suitable hormones and hormone-like compounds for use in this aspect of the invention include for example progesterones and oestrogens (both synthetic and natural) and diazacon (i.e. 20,25 diazacholesterol).

The antibody component of the protein conjugate may be obtained as described previously and may be directly chemically conjugated to a toxic component or contraceptive component. Typically this conjugation will involve the use heterobifunctional agents which result in disulphide or thioether linkages as described in the art (see for example, Hermanson, G. T. "Bioconjugate Techniques" Academic Press, London, 1996, for standard methodologies relating to the use of cross-linking reagents).

In a further embodiment where the toxic or contraceptive component is a small chemical entity the toxic compound, hormone or hormone-like compound may be encapsulated, and the capsule will be linked to an antibody or antigen-binding fragment of the invention. In one particular embodiment the capsule may be linked via chemical conjugation as discussed above. In another particular embodiment, the antibody or antigen-binding fragment of the invention may be chemically conjugated, or fused via a peptide bond, to a second binding component that binds to the capsule. For example, an antigen-binding fragment of the invention may be used to provide one specificity in a bi-specific or even multi-specific binding molecule, wherein the second (or a further) specificity is for the capsule and this second (or further specificity) is provided by a molecule (e.g. an antigen-binding fragment) which specifically binds to the capsule.

In a further aspect the antibody component of the protein conjugate is chemically conjugated to two or more toxic or contraceptive components. The further toxic or contraceptive component may be in the form of a protein or peptide moiety or in the form of a small chemical entity. Where at least one further toxic or contraceptive component is a protein or peptide moiety, the further component may be a toxin, immunogen, hormone or proteinaceous hormone mimetic as described previously. Where at least one further toxic or contraceptive component is a small chemical entity it may be a toxic compound or a hormone or hormone-like compound as described hereinbefore.

In certain embodiments of this aspect of the invention, protein conjugates are created comprising an antibody component as described herein, chemically conjugated to at least two further components, each of which confers a rodent control (i.e. toxic or contraceptive, or both) function on the protein conjugate. The second further component (and further component or components) may (each) have the same, or different rodent control functions to the first further component, and where it has (they have) the same function it (they) may have the same, or different (independently different), mode of action, as described above with respect to fusion proteins of the invention. In one particular embodiment the protein conjugate will comprise an antibody component as described hereinbefore, chemically conjugated to one or more molecules of a second toxic or contraceptive component. The site(s) of conjugation will depend on the chemistry used for the conjugation reaction. Where it is desired that two different further components are conjugated to the first (antibody) component, it may be desirable to use a different chemical method of conjugation for each further component in order to ensure that the different further components do not compete with each other for conjugation to the same site on the first component.

In yet a further aspect of the invention there is provided a rodent control agent comprising a fusion protein or protein conjugate as described hereinbefore, wherein the fusion protein or protein conjugate comprises at least two antibody components. In one embodiment each antibody component binds to the same target protein, thus increasing the probability of the rodent control agent binding to its target tissue and also potentially increasing the avidity of binding of the rodent control agent. In such embodiments the antibody components may be identical or different. Where the antibody components are different, this encompasses different antibody components which bind to the same RSE or RSPE in a target protein, or more preferably different antibody components with each antibody component binding to a different RSE or RSPE within the same target protein. In a further embodiment the rodent control agent will comprise antibody components that bind to at least two different target proteins. Embodiments comprising antibody components that bind to different RSEs or RSPEs within a single target protein and/or which comprise antibody components binding to different target proteins, may be particularly useful in delaying the onset of resistance occurring to the rodent control agent or in counteracting resistance at one of the potential target sites.

Antibodies, antigen-binding fragments, fusion proteins and protein conjugates of the invention are useful in controlling rodents, for example they may be used in methods of killing rodents or in methods of preventing breeding in rodents. Thus in a further aspect there is provided a rodent control agent comprising or consisting of an antibody, antigen-binding fragment, fusion protein or protein conjugate as described herein.

Fusion proteins and protein conjugates of the invention, wherein the second protein component is a toxin or wherein the antibody or antigen-binding fragment is conjugated to a toxic compound or protein/peptide toxin, will achieve rodent control by killing rodents (i.e. such fusion proteins and protein conjugates are rodenticidal in their mode of action). Where the antibody or antigen-binding fragment component recognises a protein expressed in the epithelium of the GI tract of rodents, the fusion protein or protein conjugate will bind to the epithelium. Depending upon the type of toxin or toxic compound present in the fusion protein/protein conjugate, the toxin or toxic compound may disrupt the cell membrane. The integrity of the epithelium of the GI tract is thus compromised, and lesions occurring in the GI tract will lead to rodent death. Alternatively, where the toxin or toxic compound mediates toxicosis through an intracellular mode of action, the bound fusion-protein or protein conjugate relies on internalisation through endocytosis. Once the fusion protein or protein conjugate has entered the cell, the toxin/toxic compound will be able to mediate toxicosis, which will ultimately result in death of the rodent.

Fusion proteins wherein the second protein component is an immunogen also require uptake into rodent cells. Once present inside the rodent cell, an immune response is mounted against the immunogen. Thus where the immunogen is an ovum or sperm specific antigen, this results in the generation of an immune response that prevents reproduction from occurring. Advantageously the antibody or antigen-binding fragment of the fusion protein will increase the amount of immunogen that is absorbed into the rodent (through endocytosis) and may also act as an adjuvant, thus increasing the likelihood of suitable immune response being mounted.

Fusion proteins and protein conjugates of the invention wherein the second protein or conjugated component is a hormone or hormone-like component similarly require uptake into rodent cells. Once present inside a rodent cell, the hormone/hormone-like compound will interfere with the hormonal control of reproduction and will thus control rodents by preventing breeding.

The rodent specificity of the antibody/antigen-binding part of the fusion proteins and protein conjugates described herein, confers several advantages on rodent control agents of the invention. The high specificity for rodent tissue means that the rodent control agent is specifically targeted to a rodent tissue thus facilitating uptake/activity of the toxic/immunogenic/hormonal component. In turn this specific targeting means that less rodent control agent is likely to be required for effective control, less rodent control agent is present in the environment, and that which is present in the environment is not specific for, and is thus less likely to be absorbed by and cause damage to, non-target species.

Rodent control agents of the invention may be formulated as a composition comprising as the active ingredient a fusion protein or protein conjugate of the invention in combination with at least one additive, diluent and/or carrier. Suitable additives include for example, compounds that act as attractants to rodents, compounds which make the composition more palatable to rodents, additional rodent control agents, and compounds which serve to stabilise or protect the rodent control agent or agents. Suitable attractant compounds include food materials such as wheat, barley, maize, sorghum, oats, rice and millet. Suitable palatability enhancing compounds for use in the invention include sweeteners, (e.g. acesulfame-K, alitame, aspartame, brazzein, cyclamate, saccharin, sucralose, sucrose, glucose, sorbitol, mannitol, xylitol, thaumatin, monellin, isomalt, and isomaltulose), vegetable or animal oils (e.g. maize, soybean and peanut oil, fish oil) and dried yeast. Suitable stability enhancing/protective compounds include those which protect or prevent the rodent control agent or agents from proteolysis or hydrolysis upon ingestion by the rodent, for example anatacids and compounds which may be used in the formation of pH release capsules.

Suitable diluents and carriers for use in compositions of the invention include those that are used as diluents and/or carriers with known rodent control agents, for example waxes, and binding agents e.g. cellulose ethers, starch, polyvinyl alcohol, polyvinyl pyrrolidone, guar gum, carrageenan, gelatin, karaya gum; xanthum gum, acacia gum, locust bean gum, tragacanth, pectin and polyacrylates.

Compositions of the invention may comprise in addition to and/or instead of any one of the aforementioned additives, diluents or carriers, an additional rodent control agents such as those mentioned hereinbefore in the introduction to the invention. In particular the present invention also includes mixtures of one or more of the novel rodent control agents described herein in combination with at least one first generation anticoagulant and/or at least one second generation anticoagulant. Preferred first generation anticoagulants for use in this aspect of the invention include the hydroxycoumarin and the indane-diones, with warfarin, coumachor, coumafuryl and coumatetralyl being particularly preferred hydroxycoumarin and pindone, diphacinone, and chlorphacinone being particularly preferred indane-diones. Preferred second generation anti-coagulants for use in this aspect of the invention include bromadiolone, brodifacoum, difenacoum, flocoumafen, and difethialone.

The present invention also encompasses mixtures of at least two of the novel rodent control agents as described hereinbefore, as well as compositions (as described above) comprising such mixtures. For example, where a rodent control agent is an antibody component that binds to an extracellular epitope of a protein that is expressed in rodents (i.e. the antibody component per se is the functional rodent control agent), this may be combined with one or more further rodent control agents, wherein the further rodent control agent comprises an antibody component and one or more toxic or contraceptive components (i.e one or more further rodent control agent(s) is(are) a fusion protein or protein conjugate as described herein). In further embodiments the mixture will comprise two or more fusion proteins and/or protein conjugates as described herein.

In one embodiment fusion proteins of the invention are produced in plants and the plant material containing the expressed fusion protein is used as bait for rodent control. Preferably the plant producing the fusion protein will be one that is capable of acting as a source of food for rodents, for example, wheat, barley, maize, sorghum, oats, rice and millet are all suitable plants for the expression of fusion proteins of the invention, according to this aspect of the invention. In one embodiment it is particularly preferred that the fusion protein will be expressed in the seeds of the plant. In this way the grain from plants expressing a fusion protein of the invention may be used directly as bait.

As mentioned hereinbefore compositions of the invention, as well as plants and/or grain containing fusion proteins of the invention, may be used as rodent control agents. Accordingly in yet a further aspect, the invention provides a method of killing rodents, comprising placing a rodent control agent in an area frequented by a rodent, such that upon ingestion by said rodent of said rodent control agent, said rodent is killed. The skilled man will also appreciate the invention also provides a method of preventing rodents from breeding comprising placing a rodent control agent in an area frequented by a rodent, such that upon ingestion by said rodent of said rodent control agent, the reproductive capability of said rodent is inhibited.

In order to test the efficacy of the rodent control agents of the invention various in vitro and in vivo studies may be conducted. An example of a suitable in vitro test is the gut loop assay as described by Heylings 1991 (Toxicol. Appl. Pharmacol. 107:482-293) and in Example 9.

Typical strategies for the in vivo evaluation of the rodenticidal properties of rodent control agents of the invention are based on the following requirements: 1) to minimise the number of animals used in tests, 2) to keep costs down, 3) to produce useful information quickly, 4) not to reject active substances that may have promise.

Initial testing will usually be conducted in the laboratory because test conditions can be carefully controlled. A cascade of test procedures is used. This cascade allows active substances to be accepted or rejected by using a sequential decision process. The usual test subjects are the Norway rat, *Rattus norvegicus*, and the House mouse, *Mus domesticus*. The Roof rat is another important test subject but as it is not available as a laboratory strain it is tested only in the latter stages of an evaluation programme. Strains of rodents that are resistant to anticoagulants may also be used in the later stages of a laboratory programme in order to test efficacy against these animals.

Rodent control agents of the invention that are active and show promise in laboratory tests may then be evaluated in the field. Field trials are conducted against all important pest rodent species in a variety of natural circumstances.

The skilled man is referred to the guideline documents that are readily available and which set out logical testing procedures for rodenticides in the laboratory (EPPO/OEPP. 1999. Laboratory tests for evaluation of the toxicity and acceptability of rodenticides and rodenticide preparations; OEPP/EPPO PP 1/113(2): 89-101) and field (EPPO/OEPP. 1999. Guidelines for the Efficacy Evaluation of Plant Protection Products: Field-tests against synanthropic rodents *Mus musculus, Rattus norvegicus, R. rattus*; OEPP/EPPO PP 1/114 (2):102-113). Recommendations are also available for test procedures that satisfy regulatory requirements in the UK (Anonymous. 2005. Guidelines on the Efficacy Data Requirements for Approval of Non-agricultural Pesticide Products Rodenticides. Health and Safety Executive, Bootle, UK. 30 pp), the European Union (Anonymous. 2002. Technical notes for guidance in support of the Annex VI of Directive 98/8/EC of the European Parliament and the Council concerning the placing of biocidal products on the market. Common principles and practical procedures for the authorisation and registration of products. European Commission, July 2002. 215 pp.) and the United States.

A typical cascade of tests which may be followed in the laboratory in order to assess the efficacy of the rodent control agents of the invention may include oral intubation tests, no-choice feeding tests, and choice feeding tests. Further details of these tests are outlined below.

Oral Intubation: initial tests to establish the potency of active substances involve the delivery of the active substance, carried in an inert liquid such as polyethylene glycol, directly to the stomach of test subjects using a gavage. Exact doses can be delivered in this way in order to determine lethal dosage percentile statistics. The test provides information on the capability of the active substance to remain active in the conditions found in the gut of the subject species and on its transfer across gut membranes. The test also provides information on the intrinsic toxicity of the active substance.

No-choice Feeding Tests: virtually all commercial rodenticide products are presented as formulated baits. The next stage of the test cascade involves the preparation of a bait containing the active substance (in this case a rodent control agent of the invention). A 'no-choice' test, in which individually-caged test subjects have only the experimental bait presented to them, is first conducted to establish whether the active substance is active when delivered as an edible bait. The test bait is normally available ad libitum. In addition to information like that obtained in oral intubation tests, no-choice feeding tests provide information on the capability of the active substance to be removed from the bait by the digestive processes of the subject species.

Choice Feeding Tests: to be capable of being controlled by an active substance in a formulated bait, rodents must consume sufficient quantities of the bait to acquire a lethal dose in the presence of alternative natural foods. Therefore, the palatability of the active substance (i.e. a rodent control agent of the invention) is an important aspect of evaluation. Choice tests are conducted in which the active substance is added to a bait base in measured concentrations. Individually-caged test subjects are then offered a choice between a test bait containing the active substance and an identical bait without the active substance. A series of such tests is conducted to establish the concentration of the active substance which is detected by the test subjects. Normally, such detection is demonstrated by an aversion to the bait containing the active substance. An important consideration in evaluation is that the concentration detected by the test subjects, and which elicits significant aversion, is lower than the concentration required to deliver a lethal dose in a test bait.

Further choice tests are conducted on experimental baits that are produced during the development of commercial formulations. These choice tests involve the presentation of the experimental formulation and a 'challenge diet'. The challenge diet is composed so that it presents a reasonably palatable alternative to the experimental formulation. A typical 'challenge diet' used in such tests is 'EPA meal'. This is a formulation comprising fixed quantities of oats, maize grits, sugar and oil. It is normal practice that an experimental formulation whose consumption comprises a minimum of 30% of the combined challenge diet and experimental formulation consumed by the test subjects would be considered a potential candidate for field trials.

Following laboratory testing, efficacy may be tested in a field environment. Rodents have complex and highly adaptive behaviours which are only fully exhibited under natural conditions. Therefore, field trials may be conducted in order to assess the effectiveness of rodenticide active substances and formulated products under field conditions. Normally, field trials are carried out against a range of target species in a variety of natural environments that are typical of those in which practical rodent control treatments might be conducted.

Field trials may be conducted at an early stage of product development using experimental formulations, not intended for commercialisation, in order to investigate natural behavioural processes in the target rodent species when they are presented with a typical bait containing the active substance.

Field trials may also be carried out subsequently on commercial bait products to demonstrate their efficacy under practical conditions.

Various aspects and embodiments of the present invention will now be illustrated in more detail by way of example. It will be appreciated that modification of detail may be made without departing from the scope of the invention.

For the avoidance of doubt, literary reference, patent application, or patent, is cited within the text of this application, the entire text of said citation is herein incorporated by reference.

EXAMPLES

Example 1

Figure 1:
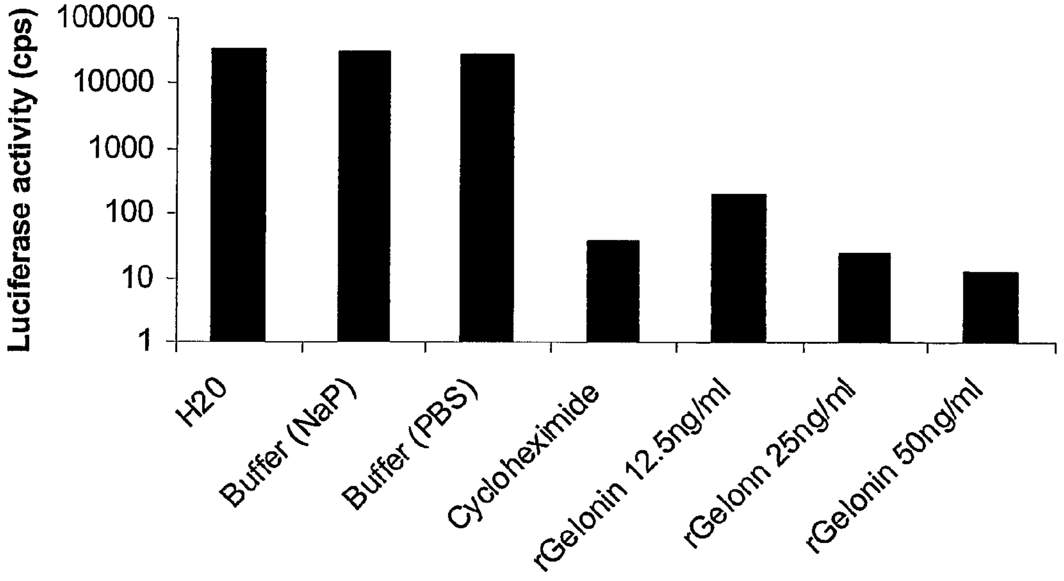
FIG. 1 Inhibition of luciferase translation by recombinant gelonin.

Generation and Preparation of RSPES 1.1 Peptide Selection and Synthesis

Potential protein targets, present on the gut epithelium of rodents are identified by literature and bioinformatic approaches. Rodent specific peptide epitopes (RSPEs) are identified in these proteins based on the following criteria: high sequence identity (preferably between 80 and 100% identity) between mouse and rat sequences and low sequence identity (preferably between 0 and 40% identity) between rodent and human sequence, and no significant hits with other species using BLAST alignments; their hydrophilicity profiles (indicator of surface probability); predictions of flexibility and secondary structure. Algorithms used for predicting hydrophilicity, flexibility and secondary structure are provided by programmes in the DNAstar and Vector NTI suites of programmes.

Once a suitable RSPE has been identified, the peptide is synthesised using Fmoc solid phase synthesis and purified to around 90% purity. The peptides shown in Table 3 below have been synthesised.

Where suitable, an N-terminal cysteine is added to the sequence to enable directed conjugation to a carrier protein. Alternatively, and where suitable, the sequence is synthesised with the N-terminal amino acid left unblocked to enable directed conjugation to a carrier protein. When not required for conjugation, the N-terminal amino acid is blocked by acetylation. In addition the C-terminal amino acid is blocked with an amide group.

TABLE 3

RSPEs that have been synthesised

| Source Protein | RSPE primary amino acid sequence | SEQ ID NO: |
|---|---|---|
| Rat oilgopeptide transporter PepT1 | VIRSRASDGCLEVKE | SEQ ID NO: 1 |
| Rat oligopeptide transporter PepT1 | CSSDFKSSNLD | SEQ ID NO: 2 |
| Rat CD155 (PVR, Tage4) | SNVNGSYREMKETGSQP | SEQ ID NO: 3 |
| Rat GTR2 (GLUT2) glucose transporter | GTDTPLIVTPAHTTP | SEQ ID NO: 4 |
| Rat CFTR chloride transporter | LKNNPVNGGNNGTKIA | SEQ ID NO: 5 |
| Rat CNT2 nucleo-side transporter | WQDKESSLRNLAK | SEQ ID NO: 6 |
| Rat CATB(O+) (slc6a14) colonic amino acid transporter | GGDMFMNISWVN | SEQ ID NO: 7 |
| Rat MDR1 multidrug resistance transporter | SFTPSRDPHSDRAIT | SEQ ID NO: 8 |
| Mouse MDR1 multi-drug resistance transporter | SFTKAEASILPSIT | SEQ ID NO: 9 |
| Rat Sucrase-Isomaltase | YNAESITNENAGLKATL | SEQ ID NO: 10 |
| Mouse GLUT7 glucose transporter | NTPHKVLKSFYN | SEQ ID NO: 11 |
| Mouse GLUT7/Rat GTR5 (GLUT5) glucose transporters | YYDRNKENIES | SEQ ID NO: 12 |
| Rat Npt2a (Slc34a1) sodium/ phosphate transporter | PETKEASTSMSRVEA | SEQ ID NO: 13 |
| IRat OATP-B (SLC21A9) organic anion transporting polypeptide | QPGPSLFPGCSEPCSCQ | SEQ ID NO: 15 |
| Rat DRA1 chloride/ anion exchanger | LSSSSAENDSMIEEKVMV | SEQ ID NO: 24 |
| Rat ENT1 equili-brative nucleoside transporter | TNQSCESTEALADPSVSL | SEQ ID NO: 26 |
| Rat GCC (Guanylyl cyclase) | VSGRFPSERS | SEQ ID NO: 27 |
| Rat PLB (Phospholipase B) | AEDLWIQAKELVRHLKDNP | SEQ ID NO: 28 |
| Rat LPH (lactase-phlorizin hydrolase) | EDAAPTASPVQS | SEQ ID NO: 29 |
| Rat AMPN (aminopeptidase N) | GSTSATTSTTNPA | SEQ ID NO: 31 |
| Rat MCDL (mucin and cadherin-like protein) | NKDILLTTVPMETERTIR | SEQ ID NO: 32 |
| Rat SCAB (amiloride-sensitive sodium channel beta-subunit) | SSNPAPGST | SEQ ID NO: 34 |

1.2 Conjugation of Peptides to BSA

Peptides containing a N-terminal cysteine residue are coupled to BSA using the hetero-bifunctional crosslinking agent m-Maleimidobenzoyl-N-hydroxylsuccinimide ester. Coupling is via the primary amines on lysine residues in BSA and sulphydryl groups on cysteine residues in the peptide as described by Kitagowa & Aikawa. J. Biochemistry Vol 79: pp 233-236 (1976).

A 25 mg/ml solution of BSA (Sigma, Poole, Dorset) is prepared in 0.2M sodium phosphate, pH 7.0 and a 25 mg/ml solution of MBS (Perbio, Cheshire) made up in dimethyl formamide (Sigma). 30 μl of MBS solution is added drop wise to 1 ml of the BSA solution with mixing and incubated in the dark at room temperature for 45 minutes. The activated BSA solution is then passed down a PD10 gel filtration column (GE Healthcare, Buckinghamshire), which had been previously equilibrated with 0.2M sodium phosphate, pH 7.0. The BSA containing fractions are identified by absorbance at 280 nm and pooled. 2 mg of peptide is dissolved in 1 ml of 50 mM sodium phosphate, pH 7.5. Sufficient activated BSA solution is added to the peptide to achieve a 30:1 molar ratio of peptide:BSA. This is incubated at room temperature for 4 hours, then overnight at 4° C. in the dark with mixing. Conjugated peptides are stored at −20° C.

Peptides that contain lysine residues or primary amines at the N-terminus are coupled to BSA using the 2-step glutaraldehyde method. Coupling is between the primary amine groups in the BSA and peptide based on the method in Bioconjugate Techniques, Academic Press 1996, pp 583-584.

A 10 mg/ml solution of BSA is made up in 0.1M sodium phosphate, 0.15M sodium chloride pH 6.8. Glutaraldehyde (Sigma) is added to a final concentration of 1.25% and the mixture incubated with mixing for 12 hours at room temperature. The activated BSA is passed down a PD10 gel filtration column, which had been previously equilibrated with PBS. The BSA containing fractions are identified by absorbance at 280 nm and pooled. 2 mg of peptide is dissolved in 1 ml of 0.5M sodium carbonate pH 9.5 and sufficient activated BSA solution is added to the peptide to achieve at least a 10:1 molar ratio of peptide:BSA. The mixture is incubated overnight at 4° C. Excess reactive sites are blocked by addition of 40 μl of 1M ethanolamine (Sigma). Conjugated peptides are stored at −20° C.

Example 2

Generation of Antibody Components

Peptides that have been synthesised and conjugated to BSA as described in Example 1 above are used to generate antibodies that bind to an extracellular epitope of a protein expressed in a rodent.

2.1 Rabbit Immunisation Protocol

New Zealand white rabbits are used for polyclonal antibody production. Rabbits are immunised with 100 μg of protein administered subcutaneously using Freunds Complete adjuvant (Sigma) for the first dose. This is followed by three booster immunisations on days 28, 56 and 84 containing 100 μg of protein administered subcutaneously in Freunds Incomplete adjuvant (Sigma). Pre-bleeds are taken prior to the initial immunisation, test bleeds are taken 10-14 days post the third dose and harvest bleeds are taken 10-14 days post the fourth dose.

For each of the following RSPEs two rabbits were immunised and polyclonal antibody sera generated: SEQ ID NO:1, SEQ ID NO: 2, SEQ ID NO: 3, SEQ ID NO: 4, SEQ ID NO: 5, SEQ ID NO: 6; SEQ ID NO: 8, SEQ ID NO: 9, SEQ ID NO: 10, SEQ ID NO: 11, SEQ ID NO:12, SEQ ID NO: 15.

For each of the following RSPEs one rabbit was immunised: SEQ ID NO: 27, SEQ ID NO: 28; SEQ ID NO: 29, SEQ ID NO: 31, SEQ ID NO: 32, SEQ ID NO: 34.

2.2 Mouse/Hamster Immunisation Protocol

Mice and hamsters are used for monoclonal antibody production, and are immunised with 20 μg of protein administered subcutaneously in Freunds Complete adjuvant for the first dose. This is followed by two immunisations of 20 μg of protein administered subcutaneously on days 28 and 56. Doses are administered in Freunds Incomplete adjuvant at day 28 and in phosphate buffered saline (PBS) at day 56. Test bleeds taken 7 days post the dose 3. At least 6 weeks after the third dose mice are boosted with 20 μg of protein administered intravenously in PBS. Spleens are harvested for fusions 4 days later.

Mice have been immunised with each of the following RSPEs and polyclonal antibody sera generated: SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO:9, SEQ ID NO: 10, SEQ ID NO: 11, SEQ ID NO: 27, SEQ ID NO: 28, SEQ ID NO: 29.

2.3 Production of Monoclonal Antibodies

Monoclonal antibodies are generated using a method based on Kohler G. & Milstein C. Nature 256, 495-497 (1975). Lymphocytes are washed from the harvested spleens with Dulbecco's Modified Eagle's Medium (DMEM, Invitrogen, Paisley) delivered by syringes with 20-gauge needles. NS0 myeloma cells (European Collection of Cell Cultures, Porton Down, Salisbury) are cultured in DMEM containing 10% (v/v) foetal bovine serum (PAA, Yeovil, Somerset), 2 mM L-glutamine, 1×HT supplement and 50 units/ml penicillin and 50 ug/ml streptomycin (all from Invitrogen) at 37° C. in 5% $CO_2$ to a density of $5\times10^5$/ml. Lymphocytes from a single spleen (approximately $2\times10^8$) will be mixed with $2\times10^7$ NS0 myeloma cells. Following centrifugation at 2000×g for 4 minutes, the cell pellet is gently resuspended and fused by dropwise addition of 1 ml of a 50% (w/v) polyethylene glycol (1500) in 75 mM HEPES buffer pH 8 (Roche, Lewes, East Sussex) over one minute. Complete culture medium (as described above) supplemented with H1 cloning supplement (Roche) is added slowly over several minutes to a final volume of 50 ml. The resulting fusion solution is cultured in five sterile microtitre cell culture plates (Nunclon, Fisher, Loughborough, Leicestershire) at 100 ul/well for 4 hours at 37° C. in 5% $CO_2$ after which, 100 ul/well of complete culture medium containing 4% (v/v) 1×HAT selection medium (Invitrogen) is added. Fourteen days post fusion the culture supernatants are assayed for peptide specific antibodies using an antibody capture enzyme-linked immunosorbant assay (ELISA) based on the methods described by Engvall E., and Perlmann P. Immunochemistry 8, 871-874 (1971); Harlow E. et al., Antibodies-A Laboratory Manual, Cold Spring Harbor Laboratory, 1988 pp. 182-183. Selected hybridoma cells are taken through at least two rounds of cloning by limiting dilution followed by re-assay, to ensure both clonality and stability of the hybridomas. Banks of frozen hybridomas are prepared in a freezing medium composed of 10% (v/v) DMSO (Sigma, Poole, Dorset) in foetal bovine serum at a freezing rate of 1° C./minute for 80 minutes followed by storage in liquid nitrogen. Production of selected monoclonal antibodies is achieved by scaling-up tissue culture.

Hybridoma fusions have been obtained using lymphocytes from the spleens of mice immunised with SEQ ID NO: 1, SEQ ID NO: 5, SEQ ID NO: 11, SEQ ID NO 6 and SEQ ID NO 27. 4 Stable monoclonal cell lines producing antibodies against the RSPE from mouse GLUT7 (SEQ ID NO 11) have been isolated, grown and frozen. 4 Stable monoclonal cell lines producing antibodies against the RSPE from Rat CFTR (SEQ ID NO 5) have been isolated. Seven positive monoclonal cell lines producing antibodies against an RSPE from Rat PepT1 (SEQ ID NO 1) have been isolated, grown and frozen.

2.4 Identification and Isolation of Antibody Components from Phage-display Libraries 2.4.1 Screening of Naïve Camelid $V_{HH}$ Phage Display Library RSPEs are prepared for screening of a naive *Llama glama* $V_{HH}$ M13 filamentous phage-display repertoire by chemical synthesis and subsequent conjugation to BSA, as described in Example 1.2 above. Screening of a phage-displayed immune binding-domain repertoire follows established procedures, such as those described by McCafferty & Johnson (in "Phage Display of Peptides and Proteins", pg 98-100, Eds. Kay, Winter & McCafferty, 1996, Academic Press, Inc.). RSPE::

BSA conjugates are adhered to the interior surface of Maxisorb Immunotubes (Nunc) by application in 50 mM sodium hydrogen carbonate pH 9.6 buffer at a concentration of 100 μg/ml and overnight incubation. Free RSPE::BSA conjugates are removed by three rinses in PBS, and then blocking of the surface by addition of PBS/2% skimmed milk protein (PBSM) and incubation at 37° C. for two hours. Following sensitisation of immunotubes with the required RSPE "panning" is effected by the addition of $10^{12}$ to $10^{13}$ phage in 4 ml of PBSM and incubating for two hours at room temperature. After this step, tube contents are aspirated and the tube is washed twenty times using PBS/0.1% Tween 20, followed by a further twenty washes with PBS. Immunotube-bound phage (representing a majority of RSPE::BSA-specific $V_{HH}$ binders) are then eluted by the addition of 1 ml 100 mM glycine pH 3.0 for 10 minutes. The solution is transferred to a fresh tube containing 0.5 ml 1M Tris-HCl pH 7.4 to neutralise. The eluted phage are then used to infect log-phase TG1 *E. coli* cells by mixing and incubating at 37° C. for 30 minutes, followed by spreading on a 24×24 cm 2×TY/2% glucose/100 μg/ml ampicillin plate (Nunc BioAssay Dish) which is then incubated at 37° C. overnight. The next day the plate is scraped to remove cells (which represent an enriched, increased, population of phagemid clones) containing sequences with binding specificity for the RSPE::BSA conjugate. In order to further screen/select clones from this population which demonstrate high affinity for the RSPE, phage particles are "rescued" by the addition of helper phage, e.g. M13-KO7, or VCS-M13. Briefly, cells from the last step are inoculated into 50 ml of 2×YT/2% glucose/100 μg/ml ampicillin in a 250 ml conical flask and incubated at 30° C. until the $OD_{600}$ is about 0.5. Helper phage are then added to provide a 1:1 ratio of helper phage to bacteria, typically $2\times10^{10}$ pfu/50 ml, followed by incubation at 37° C. for one hour. Next, cells are sedimented by centrifugation at 3000 g for 10 minutes, the supernatant is discarded, the cell pellet is resuspended and used to inoculate fresh medium in a 2 liter flask: 500 ml 2×YT/100 μg/ml ampicillin/50 μg/ml kanamycin (no glucose). This culture is incubated overnight at 30° C. with vigorous shaking and phage-$V_{HH}$ particles are then harvested by the addition of 100 ml 20% PEG/2.5M NaCl for 30 minutes at 4° C. Precipitated phage are then collected by centrifugation at 4000 g for 10 minutes and resuspended in 5 ml PBS, ready for the next round of screening. The efficiency of the selection process may be improved by the reduction of the amount of RSPE::BSA conjugate used to sensitise the immunotube at each round of panning. In addition, the selection process can be adjusted to include steps which will bias the selection of phage-$V_{HH}$ particles that exhibit certain physicochemical characteristics, such as proteolytic stability. For example, it is known that M13 phage particles are resistant to proteolysis by certain proteolytic enzymes, such as trypsin and chymotrypsin (Schwind et al, 1992, Eur. J. Biochem. 210: 431-436), and that this property can be exploited in phage-display for the selection of structurally stable variants (Kristensen & Winter, 1998, Folding & Design, 3:321-328).

In order to select individual clones which exhibit the desired affinity and selectivity for the RSPE, unique colonies on a 2×TY/2% glucose/100 μg/ml ampicillin plate (obtained from serially-diluted samples of the TG1 *E. coli* infected by eluted phage after a panning step) are picked and arrayed in a 96 well culture block containing 150 μl 2×TY/2% glucose/100 μg/ml ampicillin per well, and incubated with shaking at 30° C. until $OD_{600}$ reaches about 0.5. Helper phage are then added to each well to provide a 1:1 ratio of helper phage: bacteria, followed by further incubation with shaking at 37° C. for one hour. Then the medium is removed after sedimenting cells by centrifugation at 3000 g, and replaced with 1.5 ml of 2×YT/100 μg/ml ampicillin/50 μg/ml kanamycin (no glucose) and incubation is allowed to continue with vigorous shaking at 30° C. overnight. Phage particles are then harvested from each well using 20% PEG/2.5M NaCl for 30 minutes at 4° C. followed by centrifugation at 4000 g and resuspension in PBS. These clonal phage samples are either used in an ELISA to determine the relative binding affinity for immobilised RSPE, using an anti-phage antibody-HRP complex, or, alternatively, soluble $V_{HH}$ are expressed by infection of a non-amber suppressor *E. coli* host, (such as strain HB2151) with the phage. 96 well culture and expression of soluble, secreted $V_{HH}$ is then made possible using IPTG induction, and either crude culture medium (containing soluble $V_{HH}$), or, IMAC-purified $V_{HH}$ (by virtue of an integral hexa-histidine tag) is used in ELISA to determine binding to immobilised RSPE. A suitable detection antibody in this case is 9E10-HRP (Roche Molecular Biochemicals) which detects the c-Myc tag present on the soluble $V_{HH}$ protein.

Initially the following RSPEs are screened as RSPE::BSA conjugates against a naïve Camelid phage display library as described above: RSPE with SEQ ID NO 5, RSPE with SEQ ID NO: 6, RSPE with SEQ ID NO: 11 and RSPE with SEQ ID NO 27. The $V_{HH}$ clones identified from this screen are then used in the production of fusion proteins and antibody conjugates as described herein.

2.5 Cloning and Expression of Recombinant Antibody Binding Domains

To exemplify the process of creating single chain antibodies, more specifically scFv, the SV63 mouse monoclonal antibody (MAb) (recognising a cell-surface epitope from human alkaline phosphatase expressed by certain colorectal tumours) from the hybridoma HB-8766 (American Type Culture Collection; Rettig et al, 1989, U.S. Pat. No. 4,851,332) is used as a model cell-surface antigen binding protein. In order to derivatise an scFv molecule from this IgG1 MAb the Fv sequences are cloned from the hybridoma using RT-PCR with rodent Fv and constant domain-specific primer sets as described in the literature (e.g. Dubel et al. 1994, Journal of Immunological Methods 175: 89-95; McCafferty & Johnson in "Phage Display of Peptides and Proteins", pg 95, Eds. Kay, Winter & McCafferty, 1996, Academic Press, Inc.), using the modifications to individual primers as specified in the literature. The sequences of the primers used in this Example are given in Table 4 below.

TABLE 4

Primers used in cloning the SV63 scFvs from hybridomas ATCC HB-8766

| Primer | Sequence 5' to 3' | SEQ ID |
|---|---|---|
| RoPro-9 | AGGTSCAGCTGCAGSAGTCWGG | SEQ ID NO: 37 |
| RoPro-28 | CCAGGGGCCAGTGGATAGACAGATGGGGGTGTCGTT<br>TT | SEQ ID NO: 38 |

TABLE 4-continued

| Primers used in cloning the SV63 scFvs from hybridomas ATCC HB-8766 | | |
|---|---|---|
| Primer | Sequence 5' to 3' | SEQ ID |
| RoPro-6 | GAGGTGAAGCTGCAGGAGTCAGGACCTAGCCTGGTG | SEQ ID NO: 39 |
| RoPro-25 | TGAGGAGACGGTGACCGTGGTCCCTTGGCCCC | SEQ ID NO: 40 |
| RoPro-3 | GGTGATATCGTKCTCACYCARTCTCCAGCAAT | SEQ ID NO: 41 |
| RoPro-4 | GGGAAGATGGATCCAGTTGGTGCAGCATCAGC | SEQ ID NO: 42 |
| scFv oligo 1 | AGCCCGCCATGGCCGATATCGTTCTCACTCAATC | SEQ ID NO: 43 |
| scFv oligo 2 | CGCCAGAGCCACCGCCACCGCTACCGCCACCGCCCT TGATCTCCAGTTTGGTGCCTC | SEQ ID NO: 44 |
| scFv oligo 3 | AGCGGTGGCGGTGGCTCTGGCGGTGGCGGTAGCGA GGTCCAGCTGCAGGAGTCTGG | SEQ ID NO: 45 |
| scFv oligo 4 | CTATGAATTCAGTGGTGGTGGTGGTGGTGCTTGTCGT CGTCGTCCTTGTAGTCTGAGGAGACTGTGAGAGTGG TGC | SEQ ID NO: 46 |
| scFv oligo 5 | AGCCGGCCATGGCCGAGGTCCAGCTGCAGGAGTCTG | SEQ ID NO: 47 |
| scFv oligo 6 | CGCCAGAACCAGCTCCGCCGCTTCCGCCACCGCCTG AGGAGACTGTGAGAGTGGTGCC | SEQ ID NO: 48 |
| scFv oligo 7 | AGCGGCGGAGGTGGTTCTGGCGGTGGCGGAAGCGA TATCGTTCTCACTCAATCTC | SEQ ID NO: 49 |
| soFv oligo 8 | GTATGAATTCAGTGGTGGTGGTGGTGGTGCTTGTCGT CGTCGTCCTTGTAGTCCTTGATCTCCAGTTTGGTGCC TC | SEQ ID NO: 50 |

2.5.1 Isolation of Hybridoma RNA and cDNA Synthesis

Hybridoma cells ($10^7$) were centrifuged and resuspended in 1 ml of Trizol™ and 200 μl of chloroform. The sample was mixed vigorously for 15 minutes at room temperature and then centrifuged at 12000 g for 15 minutes at 4° C. The aqueous layer was removed and an equal amount of isopropanol is added. The sample was centrifuged at 12,000 rpm for 15 minutes at 4° C. to precipitate the RNA, which was washed in 70% ethanol and then resuspended in RNase free water.

Traces of genomic DNA were removed from RNA by treatment with RNase free DNase in a 10 μl reaction containing 5 μl RNA, 0.1 U RNase free DNase I (Ambion) and 1 U RNasin. The mixture was placed at 37° C. for 30 minutes followed by an incubation at 80° C. for 5 minutes.

The DNase I treated RNA was then used in an Accuscript (Stratagene) reaction under the manufacturer's standard conditions (1.5 μl RNA, 50 μl total reaction volume, oligo-dT primer) to produce $1^{st}$ strand cDNA.

2.5.2 Isolation and Cloning of SV63 $V_H$ Region

PCR was carried out using 1 μl of the oligo-dT primed $1^{st}$ strand cDNA derived from SV63 RNA as template and oligonucleotides RoPro-9 (SEQ ID NO: 37) and RoPro-28 (SEQ ID NO: 38).

The Roche GC-RICH PCR System was used with GC-RICH resolution buffer at a concentration of 0.5M in a reaction volume of 25 μl.

The reaction was carried out in a Stratagene Robocycler with the following cycling conditions:

| Cycle 1-5 | Cycle 6-35 | Final extension |
|---|---|---|
| 94° C. 30 sec | 94° C. 30 sec | |
| 54° C. 30 sec | 60° C. 30 sec | |
| 72° C. 60 sec | 72° C. 60 sec | 72° C. 300 sec |

The yield of PCR product was very low from this reaction. Hence, a second PCR was carried out to further amplify molecules produced.

Using the 2 μl of the PCR product from the reaction described above as template, two reactions were set up using the following oligonucleotide primer pairs: i) RoPro-6 (SEQ ID NO 39, less specific than RoPro-9 (SEQ ID NO 37) and RoPro-25 (SEQ ID NO: 40, 3' nested) and ii) RoPro-9 (SEQ ID NO: 37) and RoPro-28 (SEQ ID NO: 38). The PCR was carried out as described above.

When samples of the above reactions were run on a 1% agarose/TBE gel and stained with ethidium bromide, both PCRs contained DNA fragments of approximately 400 bp. The PCR product resulting from reaction 2 above was isolated and purified using Geneclean Spin kit and cloned into pCRTOPO BluntII (Invitrogen).

Eight TOPO clones were fully characterised by DNA sequencing, one of these clones had the characteristics of a typical (but unique) $V_H$ sequence as determined by BLASTP analysis of the UniProt/IPI-databases.

2.5.3 Isolation and Cloning of SV63 $V_L$ Region

PCR was carried out using 20 of the oligo-dT primed $1^{st}$ strand cDNA derived from SV63 RNA as template and oligonucleotides RoPro-3 (SEQ ID NO: 41) and RoPro-4 (SEQ ID NO: 42). Stratagene Pfu Ultra DNA polymerase was used in a reaction volume of 50 μl and the reaction was carried out in an MJ Research Dyad thermocycler using the following cycling conditions: 95° C., 1 min then [95° C., 1 min; 52° C., 1 min; 68° C., 3 mins] for 40 cycles, followed by a final extension of 68° C., 10 mins.

A sample of the above reaction was analysed on a 1% agarose/TBE gel and stained with ethidium bromide, a fragment of approximately 350 by was observed. This PCR product was isolated and purified using QiaQuick (Qiagen) gel elution and cloned into pCRTOPOBlunt II (Invitrogen).

Five TOPO clones were fully characterised by DNA sequencing, four of these clones were identical and had the characteristics of a typical (but unique) $V_L$ sequence as determined by BLASTP analysis of the UniProt/IPI databases. One of the five clones contained a sequence that was identical to the MOPC21 kappa light chain variable sequence (Swissprot: P01634), an irrelevant sequence amplified from the myeloma fusion partner used in the creation of the hybridoma.

2.5.4 Assembly of $V_H$ & $V_L$ Sequences into scFv Constructs

PCR-overlap extension (also known as "Splice-overlap extension"; SOE) was used to create two orientations of SV63 scFv: (i) $V_H$-[$Gly_4$Ser]$_3$ linker-$V_L$ and (ii) $V_L$-[$Gly_4$Ser]$_3$ linker-$V_H$), each containing N-terminal PelB leader sequences and C-terminal FLAG and hexa-histidine tags in the *E. coli* expression vectors pDGF (derived from the NEB vector pMALc-2, pDGF contains all of the features of pMALc-2 except for the sequence encoding the maltose binding protein, which has been excised) and pIMS147 (Hayhurst & Harris, 1999, Protein Expression and Purification 15: 336-343). Table 5 below indicates the oligonucleotide primers used and their purpose.

TABLE 5

Primers used in the assembly of $V_H$ and $V_L$ sequences into scFv constructs

| Primer | Purpose | SEQ ID NO: |
|---|---|---|
| scFv oligo 1 | SV63 scFv VL::VH orientation PelB:Vl forward primer | 43 |
| scFv oligo 2 | SV63 scFv VL::VH orientation Vl:GlySer reverse primer | 44 |
| scFv oligo 3 | SV63 scFv VL::VH orientation GlySer:Vh forward primer | 45 |
| scFv oligo 4 | SV63 scFv VL::VH orientation Vh:FLAG:His reverse primer | 46 |
| scFv oligo 5 | SV63 scFv VH::VL orientation PelB:Vh forward primer | 47 |
| scFv oligo 6 | SV63 scFv VH::VL orientation Vh:GlySer reverse primer | 48 |
| scFv oligo 7 | SV63 scFv VH::VL orientation GlySer:Vl forward primer | 49 |
| scFv oligo 8 | SV63 scFv VH::VL orientation Vl:FLAG:His reverse primer | 50 |

To create the $V_L$-[$Gly_4$Ser]$_3$ linker-$V_H$ scFv sequence, PCR was performed in two steps. The first step consisted of two reactions using i) scFv oligo's 1 & 2 (SEQ ID NOs: 43 and 44, respectively) and a pCRTOPOBluntII SV63 $V_L$ clone as template to amplify the 5' half of the construct; ii) scFv oligo's 3 & 4 (SEQ ID NOs: 45 and 46 respectively) and a pCRTOPOBluntII SV63 $V_H$ clone as template to amplify the 3' half of the construct. The second step used SOE to join the two fragments from (i) and (ii) by annealing their complementary 3' and 5' termini (respectively) and extending to full-length product by the addition of polymerase, with subsequent amplification using scFv oligo's 1 & 4 (SEQ ID NOs: 43 and 46 respectively).

The $V_H$-[$Gly_4$Ser]$_3$ linker-$V_L$ scFv sequence was created in a similar approach. The first step consisted of two reactions using i) scFv oligo's 5 & 6 (SEQ ID NOs: 47 and 48, respectively) and a pCRTOPOBluntII SV63 $V_H$ clone as template to amplify the 5' half of the construct; ii) scFv oligo's 7 & 8 (SEQ ID NOs: 49 and 50, respectively) and a pCRTOPOBluntII SV63 $V_L$ clone as template to amplify the 3' half of the construct. The second step used SOE to join the two fragments from (i) and (ii) by annealing their complementary 3' and 5' termini (respectively) and extending to full-length product by the addition of polymerase, with subsequent amplification using scFv oligo's 5 & 8 (SEQ ID NOs 47 and 50, respectively).

First step reactions were performed using a Roche GC RICH kit and the manufacturer's conditions with GC-RICH resolution buffer at a concentration of 0.5M in a reaction volume of 25 μl. The reactions were carried out in a Stratagene Robocycler with the following cycling conditions:

| Cycle 1-2 | Cycle 3-27 | Final extension |
|---|---|---|
| 94° C. 30 sec | 94° C. 30 sec | |
| 54° C. 30 sec | 65° C. 30 sec | |
| 72° C. 60 sec | 72° C. 60 sec | 72° C. 300 sec |

Samples of the above reactions were analysed on a 1% agarose/TBE gel and stained with ethidium bromide and these revealed that all four expected DNA fragments had been produced.

Second step SOE reactions were carried out by mixing the appropriate fragment pairs in approximately equal amounts in Roche GC RICH kit reactions using the manufacturer's conditions with GC-RICH resolution buffer at a concentration of 0.5M in a volume of 25 μl. Reactions were carried out using the 2 step cycling conditions below:—

| Cycle 1-2 |
|---|
| 94° C. 30 sec |
| 65° C. 30 sec |
| 72° C. 60 sec |

This reaction acts as a primer extension producing full length fusions. Oligonucleotide primers were then added to PCR amplify the full length molecules using the cycling conditions below.

| Cycle 3-15 | Final extension |
|---|---|
| 94° C. 30 sec | |
| 65° C. 30 sec | |
| 72° C. 60 sec | 72° C. 300 sec |

When samples of the above SOE reactions were analysed on a 1% agarose/TBE gel and stained with ethidium bromide, both reactions were shown to contain DNA fragments of approximately 750 by (the expected size).

The SOE products were isolated and purified using Geneclean Spin kits and cloned into pCRTOPO BluntII (Invitrogen). For each SOE product ($V_H$->$V_L$ and $V_L$->$V_H$) a TOPO clone was fully characterised by DNA sequencing. pDGF expression constructs (pDGF-SV63-VHVL and pDGF-SV63-VLVH) were then created by the excision of the scFv sequences from pCRTOPOBluntII using NdeI and EcoRI, and subsequent ligation into similarly prepared pDGF vector backbone DNA. pIMS147 expression constructs (pIMS-SV63-VHVL and pIMS-SV63-VLVH) were also generated by excision of the scFv sequences from pCRTOPOBluntII using NcoI and EcoRI, and subsequent ligation into similarly prepared pIMS147 vector backbone DNA. Ligation reactions were transformed into *E. coli* TOP10 cells (Invitrogen) following the manufacturers instructions and transformants identified. Correct pIMS147-SV63 scFv and pDGF-SV63 scFv clones were identified by DNA sequence analysis to confirm maintenance of reading frame and accuracy of sequence.

2.5.5 Expression of Recombinant scFv Protein in *E. coli* pIMSSV63-scFv *E. coli* TOP10 clones were tested for expression of soluble scFv protein following the guidelines described by Charlton (in "Antibody Engineering: methods & protocols" pg 245-254, Ed. B.K.C. Lo, Humana Press, 2004). Briefly, overnight cultures of selected clones were used to inoculate 500 ml of 2TY(amp/glu) (16 g Bacto-peptone/5 g Yeast extract/5 g NaCl/2% (w/v) glucose in 1 liter, pH 7.5, +100 μg/ml ampicillin) in 2.5l flasks, which were then incubated at 37° C. and 250 rpm until the $OD_{600}$ reached approximately 0.8. At this point, the cells were harvested by centrifugation at 3000 g and transferred to 500 ml fresh 2TY(amp/suc) (16 g Bacto-peptone/5 g Yeast extract/5 g NaCl/0.4M sucrose in 1 liter, pH 7.5, +100, μg/ml ampicillin) in 2.5 l flasks. Incubation then commenced at 30° C. and 250 rpm for 1 hour, prior to the addition of IPTG to a final concentration of 1 mM. Incubation, then proceeded for a further 16 hours at which point cells and media were harvested and analysed for the presence of recombinant scFv using SDS-PAGE and Western blot procedures. Western analysis using the anti-FLAG M2-HRP antibody (Sigma) in combination with BM POD chromogenic substrate solution (Roche) indicated good levels of expression of recombinant protein (of the expected size molecular weight of approx 30 kDa) in both soluble cell lysate and media samples for both orientations of the scFv.

Recombinant scFv protein was purified using IMAC column chromatography and tested for functionality by competition with parental SV63 MAb for antigen binding in an immunocytochemical assay using Caco2Bbe1 cells (CRL-2102, American Type Culture Collection). Both orientations of the scFv were observed to inhibit the binding of parental SV63 MAb to the cell surfaces, indicating maintenance of the antigen binding surface in the engineered scFv.

Example 3

Antibody Purification 3.1 Preparation of Peptide Affinity Columns

For the purification of peptide-specific antibodies from polyclonal sera, peptide affinity columns are produced. Depending on the N-terminal residue of the peptide, one of two methods for column preparation was used. These used either SulfoLink or AminoLink coupling gel as the affinity matrix.

SulfoLink coupling gel (Perbio) allows covalent immobilisation of sulphydryl-containing peptides to an agarose gel support for use in affinity purification procedures. RSPEs are coupled to this gel, using a protocol supplied by the manufacturer and summarised below.

10 ml of SulfoLink gel slurry (5 ml gel bed volume) is equilibrated to room temperature. The gel slurry is poured into a column and equilibrated with 20 ml of coupling buffer (50 mM Tris, 5 mM EDTA pH 8.5) (Sigma). 1 mg of synthetic peptide is dissolved in 5 ml of coupling buffer and added to the column. The column is sealed and incubated at room temperature with mixing by inversion for 15 minutes, then the gel is allowed to settle for 30 minutes. Excess buffer is allowed to drain, before the column is washed with 15 ml of coupling buffer. Non-specific binding sites are blocked with 5 ml of 50 mM L-cysteine hydrochloride (Sigma) in coupling buffer. The column is sealed and incubated with and without mixing, as described above. The column is washed with 30 ml of 1M sodium chloride (Sigma) and prepared for storage by applying 10 ml of degassed PBS pH 7.2 containing 0.05% sodium azide (Sigma). The coupled column is stored at 4° C.

AminoLink coupling gel (Perbio) allows covalent immobilisation of peptides via the primary amine to an agarose gel support for use in affinity purification procedures. RSPEs are coupled to this gel using a protocol supplied by the manufacturer and summarised below.

10 ml of AminoLink gel slurry (5 ml gel bed volume) is equilibrated to room temperature. The gel slurry is poured into the column and equilibrated with 20 ml of coupling buffer (0.1M sodium phosphate, pH 7.5, 0.05% sodium azide. 1 mg of synthetic peptide is dissolved in 5 ml of coupling buffer. 250 μl of 1M sodium cyanoborohydride made up in 0.01M sodium hydroxide (Sigma) is then added to the peptide solution, which is poured into the column. The column is sealed and incubated at room temperature with mixing by inversion for 6 hours. The column is allowed to stand and then the supernatant is removed. 5 ml of 1M Tris-HCl pH 7.4 (Sigma) and 250 μl of 1M sodium cyanoborohydride made up in 0.01M sodium hydroxide is added. The column is sealed and incubated at room temperature with mixing by inversion for 30 minutes. The column is washed with 30 ml of 1M sodium chloride and prepared for storage by applying 10 ml of degassed PBS containing 0.05% sodium azide. The coupled column is stored at 4° C.

3.2 Purification of Peptide-specific Antibodies from Polyclonal Sera

Polyclonal rabbit sera are centrifuged at 2500×g for 10 minutes, filtered using 0.45 micron membranes and then diluted 1:1 with PBS. The peptide affinity column is allowed to reach room temperature and then equilibrated with 4 column volumes of PBS. A prepared serum solution is added to the column with the flow through being reapplied to the column. The column is washed with 6 column volumes of PBS. Peptide-specific antibody is eluted by applying 0.1M glycine-HCl pH 3.0 (Sigma) to the column and collecting 1 ml fractions in tubes containing 0.1 ml of 1M Tris-HCl pH 8.0. Fractions containing protein are then identified by absorbance at 280 nm and pooled. Purified antibody is dialysed into PBS using a Slide-a-Lyser cassette with 10,000 molecular weight cut-off (Perbio) and stored at −20° C. Meanwhile, the column is regenerated with 3 column volumes of 0.1M glycine-HCl pH 2.5, followed by 8 column volumes of PBS.

3.2 Purification of Monoclonal Antibodies

Monoclonal IgG is purified from culture supernatant by protein G affinity chromatography using a HiTrap protein G HP 1 ml column (GE Healthcare). Culture supernatant is centrifuged at 2500×g for 10 minutes and filtered using 0.45 micron membranes before use. The maximum flow rate is 1 ml/minute throughout. The column is equilibrated with 10 column volumes of PBS pH 7 and the sample is loaded. The column is washed with 10 column volumes of PBS. Antibody is eluted by applying 0.1M glycine-HCl pH 3.0 (Sigma) to the column and collecting 1 ml fractions in tubes containing 0.1 ml of 1M Tris-HCl pH 8.0. Fractions containing protein are then identified by absorbance at 280 nm and pooled. Purified antibody is dialysed into PBS using a Slide-a-Lyser cassette with 10,000 molecular weight cut-off (Perbio) and stored at −20° C. Meanwhile the column is regenerated with 10 column volumes of 0.1M glycine pH 2.5, washed with 10 column volumes of PBS and stored in 20% ethanol at 4° C.

Example 4

Antibody Characterisation 4.1 Titration of Anti-peptide Antibodies by Enzyme-linked Immunosorbent Assay (ELISA)

Sera obtained from rabbits, mice or hamsters immunised with peptide conjugates are assayed by enzyme-linked immunosorbent assay (ELISA) to determine the relative magnitude of the antibody responses, based on the methods described by Engvall E., and Perlmann P. Immunochemistry 8, 871-874 (1971); Harlow E. et al., Antibodies-A Laboratory Manual, Cold Spring Harbor Laboratory, 1988 pp. 182-183.

Peptide solutions at 2 μg/ml in 35 mM sodium bicarbonate, 15 mM sodium carbonate pH 9.5 are added at 100 μl/well to 96-well microtitre plates and incubated for at least four hours at 4° C. Plates are then washed three times with PBS, 0.05% Tween 20 (PBST) (Sigma). Remaining binding sites are blocked with 200 μl well of PBS containing 1% skimmed milk powder (Marvel, Premier Foods, St Albans) for 30 minutes at room temperature. After washing as above, PBST is added to the plates at 100 ul/well. Initial dilutions of sera are added to duplicate wells in column 1 and then double-diluted across the wells of the plates, leaving the wells in column 12 containing PBST only. The plates are incubated at room temperature for 2 hours. After further washes as above, the plates are incubated at room temperature for 1 hour with the appropriate anti-species conjugated antibody diluted to 1/10,000 in PBST. Rabbit sera samples are incubated with goat anti-rabbit IgG horseradish peroxidase (HRP) conjugate (Sigma); hamster sera with rabbit anti-Syrian hamster IgG HRP conjugate (Stratec, Soham, Cambridgeshire) and mouse sera samples will be incubated with both rabbit anti-mouse IgG HRP conjugate (Sigma) and goat anti-mouse IgG Fc fragment HRP conjugate (Sigma). Substrate solution is prepared by diluting one tablet containing 1 mg of 3,3',5,5' tetramethylbenzidine dihydrochloride (Sigma) in 10 ml of 24 mM citric acid, 60 mM sodium phosphate pH 5.0 and adding 2 μl of 30% solution of hydrogen peroxide (Sigma). After further washing, fresh substrate solution is added to the plates at 100 ul/well and the plates are left in the dark at room temperature for 30 minutes. The resulting colour development is stopped by adding 50 ul/well of 3M sulphuric acid. The optical density of the plate is then read at 450 nm using a microtitre plate reader.

4.2 ELISA Results 4.2.1 Polyclonal Anti-sera from Rabbits

Sera taken post-third dose from rabbits immunised with RSPEs from the following target proteins (see Example 2.1 above) Rat oligopeptide transporter PepT1, Rat CD155 (PVR-poliovirus receptor; Tage4), Rat GTR2, Rat CFTR, Rat CNT2, Rat MDR1, Mouse MDR1, Rat sucrase-isomaltase, Mouse GLUT 7, Rat GTR5, Rat OATP-B, Rat GCC, Rat PLB, Rat LPH, Rat AMPN, Rat MCDL, and Rat SCAB were assayed by peptide ELISA as described in Example 4.1 above. Test and pre-immune sera from each rabbit were assayed by titration against their immunising peptide. The immune response was assessed by calculating 50% binding titre values (dilution required to reduce maximum signal to 50%). The results are summarised in Table 6 below.

TABLE 6

ELISA results showing that rabbit polyclonal antibodies against the specified RSPEs have been generated.

| SOURCE PROTEIN | Immunising RSPE | Serum | 50% Binding Titre (fold dilution) |
|---|---|---|---|
| Rat oligopeptide transporter PepT1 | SEQ ID NO: 1 | Rabbit 1 (pre-immune) | — |
| | | Rabbit 1 (test) | >500,000 |
| | | Rabbit 2 (pre-immune) | — |
| | | Rabbit 2 (test) | >500,000 |
| Rat oligopeptide transporter PepT1 | SEQ ID NO: 2 | Rabbit 1 (pre-immune) | — |
| | | Rabbit 1 (test) | 33,000 |
| | | Rabbit 2 (pre-immune) | — |
| | | Rabbit 2 (test) | 5000 |
| Rat CD155 (PVR, Tage4) | SEQ ID NO: 3 | Rabbit 1 (pre-immune) | — |
| | | Rabbit 1 (test) | 15,000 |
| | | Rabbit 2 (pre-immune) | — |
| | | Rabbit 2 (test) | 5,000 |
| Rat GTR2 (GLUT2) glucose transporter | SEQ ID NO: 4 | Rabbit 1 (pre-immune) | — |
| | | Rabbit 1 (test) | 55,000 |
| | | Rabbit 2 (pre-immune) | — |
| | | Rabbit 2 (test) | 40,000 |
| Rat CFTR chloride transporter | SEQ ID NO: 5 | Rabbit 1 (pre-immune) | — |
| | | Rabbit 1 (test) | 95,000 |
| | | Rabbit 2 (pre-immune) | — |
| | | Rabbit 2 (test) | 44,000 |
| Rat CNT2 nucleoside transporter | SEQ ID NO: 6 | Rabbit 1 (pre-immune) | — |
| | | Rabbit 1 (test) | 50,000 |
| | | Rabbit 2 (pre-immune) | — |
| | | Rabbit 2 (test) | 50,000 |
| Rat MDR1 multidrug resistance transporter | SEQ ID NO: 8 | Rabbit 1 (pre-immune) | — |
| | | Rabbit 1 (test) | 35,000 |
| | | Rabbit 2 (pre-immune) | — |
| | | Rabbit 2 (test) | 64,000 |
| Mouse MDR1 multidrug resistance transporter | SEQ ID NO: 9 | Rabbit 1 (pre-immune) | — |
| | | Rabbit 1 (test) | 41,000 |
| | | Rabbit 2 (pre-immune) | — |
| | | Rabbit 2 (test) | 8,000 |

TABLE 6-continued

ELISA results showing that rabbit polyclonal antibodies against the specified RSPEs have been generated.

| SOURCE PROTEIN | Immunising RSPE | Serum | 50% Binding Titre (fold dilution) |
|---|---|---|---|
| Rat sucrase-isomaltase | SEQ ID NO: 10 | Rabbit 1 (pre-immune) | — |
| | | Rabbit 1 (test) | 31,000 |
| | | Rabbit 2 (pre-immune) | — |
| | | Rabbit 2 (test) | 7,000 |
| Mouse GLUT7 glucose transporter | SEQ ID NO: 11 | Rabbit 1 (pre-immune) | — |
| | | Rabbit 1 (test) | 11,000 |
| | | Rabbit 2 (pre-immune) | — |
| | | Rabbit 2 (test) | 34,000 |
| Mouse GLUT7/Rat GTR5 (GLUT5) glucose transporters | SEQ ID NO: 12 | Rabbit 1 (pre-immune) | — |
| | | Rabbit 1 (test) | 30,000 |
| | | Rabbit 2 (pre-immune) | — |
| | | Rabbit 2 (test) | 34,000 |
| Rat OATP-B (SLC21A9) organic anion transporting polypeptide | SEQ ID NO: 15 | Rabbit 1 (pre-immune) | — |
| | | Rabbit 1 (test) | 66,000 |
| | | Rabbit 2 (pre-immune) | — |
| | | Rabbit 2 (test) | 12,000 |
| Rat GCC (guanylyl cyclase) | SEQ ID NO: 27 | pre-immune | — |
| | | test | 90,000 |
| Rat PLB (phospholipase B) | SEQ ID NO: 28 | pre-immune | — |
| | | test | 170,000 |
| Rat LPH (lactase-phlorizin hydrolase) | SEQ ID NO: 29 | pre-immune | — |
| | | test | 35,000 |
| Rat AMPN (aminopeptidase N) | SEQ ID NO: 31 | pre-immune | — |
| | | test | 220,000 |
| Rat MCDL (mucin and cadherin-like protein) | SEQ ID NO: 32 | pre-immune | — |
| | | test | 16,000 |
| Rat SCAB (amiloride-sensitive sodium channel beta-subunit) | SEQ ID NO: 34 | pre-immune | — |
| | | test | 18,000 |

Sera from each of the test bleeds was affinity purified as described in Example 3.2 and then tested by ELISA as described previously. The results are given in Table 7 below.

TABLE 7

ELISA results for affinity-purified antibodies obtained from rabbit test sera.

| Immunising RSPE | Serum sample | Elution Volume (ml) | Concentration of Eluate (mg/ml) | 50% Binding Titre (fold dilution) |
|---|---|---|---|---|
| SEQ ID NO: 1 | Rabbit 1 | 10 | 0.47 | $1 \times 10^7$ |
| | Rabbit 2 | 10 | 0.47 | 930,000 |
| SEQ ID NO: 2 | Rabbit 1 | 3.5 | 0.08 | 32,000 |
| | Rabbit 2 | 2 | 0.12 | 3,000 |
| SEQ ID NO: 3 | Rabbit 1 | 3 | 0.25 | 8,000 |
| | Rabbit 2 | 3.5 | 0.26 | 6,000 |
| SEQ ID NO: 4 | Rabbit 1 | 7.25 | 0.14 | 18,000 |
| | Rabbit 2 | 4 | 0.21 | 5,000 |
| SEQ ID NO: 5 | Rabbit 1 | 5.5 | 0.72 | 51,000 |
| | Rabbit 2 | 4.5 | 0.32 | 19,000 |
| SEQ ID NO: 6 | Rabbit 1 | 7 | 0.52 | 47,000 |
| | Rabbit 2 | 6 | 0.35 | 16,000 |
| SEQ ID NO: 8 | Rabbit 1 | 5.5 | 0.64 | 42,000 |
| | Rabbit 2 | 9 | 0.65 | 31,000 |
| SEQ ID NO: 9 | Rabbit 1 | 5 | 0.26 | 33,000 |
| | Rabbit 2 | 3.25 | 0.20 | 8,000 |
| SEQ ID NO: 10 | Rabbit 1 | 6 | 0.35 | 16,000 |
| | Rabbit 2 | 4.5 | 0.16 | 2,000 |
| SEQ ID NO: 11 | Rabbit 1 | 5.5 | 0.66 | 7,000 |
| | Rabbit 2 | 9 | 0.94 | 7,000 |
| SEQ ID NO: 12 | Rabbit 1 | 8 | 0.23 | 30,000 |
| | Rabbit 2 | 5 | 0.09 | 34,000 |
| SEQ ID NO: 15 | Rabbit 1 | 9.5 | 0.31 | 66,000 |
| | Rabbit 2 | 6 | 0.19 | 12,000 |
| SEQ ID NO: 27 | Rabbit 1 | 6 | 0.29 | 20,000 |
| SEQ ID NO: 28 | Rabbit 1 | 6 | 0.66 | 19,000 |
| SEQ ID NO: 29 | Rabbit 1 | 6 | 0.20 | 12,000 |
| SEQ ID NO: 31 | Rabbit 1 | 7 | 0.18 | 10,000 |

TABLE 7-continued

ELISA results for affinity-purified antibodies obtained from rabbit test sera.

| Immunising RSPE | Serum sample | Elution Volume (ml) | Concentration of Eluate (mg/ml) | 50% Binding Titre (fold dilution) |
|---|---|---|---|---|
| SEQ ID NO: 32 | Rabbit 1 | 3 | 0.16 | 8,000 |
| SEQ ID NO: 34 | Rabbit 1 | 5 | 0.18 | 5,000 |

Harvest bleeds for rabbits immunised with the RSPE from the Rat CNT2 nucleoside transporter were also affinity purified and tested by ELISA. The harvest bleed from rabbit 1 was eluted in 36.5 ml at a concentration of 0.86 mg/ml and the 50% binding titre was assayed at 1 in 47,000. The harvest bleed from rabbit 2 was eluted in 27.5 ml at a concentration of 0.57 mg/ml and the 50% binding titre was assayed at 1 in 44,000.

The affinity purified polyclonal antibodies from rabbit 1 were further purified using a Protein A column (Amersham), dialysed against phosphate buffered saline (PBS) and tested by ELISA. This resulted in 13 mls of further purified polyclonal IgG against the CNT2 derived RSPE (SEQ ID NO: 6), which had a concentration of 1.97 mg/ml and a 50% binding titre of 1 in 90,000.

4.2.2 Polyclonal Anti-sera from Mice

Sera taken post-third dose from mice immunised with RSPEs from the following target proteins (see Example 2.2 above), Rat oligopeptide transporter PepT1, Rat CD155 (PVR-poliovirus receptor; Tage4), Rat GTR2, Rat CFTR, Rat CNT2, Rat MDR1, Mouse MDR1, Rat sucrase-isomaltase, Mouse GLUT 7, Rat GCC, Rat PLB, and Rat LPH, were assayed by peptide ELISA as described in Example 4.1 above. Test serum from each mouse was assayed by titration against the immunising peptide. The immune response was assessed by calculating 50% binding titre values (dilution required to reduce maximum signal to 50%). The results are summarised in Table 8 below.

TABLE 8

ELISA results showing that mouse polyclonal antibodies against the specified RSPEs have been generated.

| SOURCE PROTEIN | Immunising RSPE | Mouse serum sample | 50% Binding Titre (fold dilution) |
|---|---|---|---|
| Rat oligopeptide transporter PepT1 | SEQ ID NO: 1 | 1 | >100,000 |
| | | 2 | 70,000 |
| | | 3 | 70,000 |
| | | 4 | >100,000 |
| Rat oligopeptide transporter PepT1 | SEQ ID NO: 2 | 1 | — |
| | | 2 | 10,000 |
| | | 3 | — |
| | | 4 | — |
| Rat CD155 (PVR, Tage4) | SEQ ID NO: 3 | 1 | 3,000 |
| | | 2 | 62,000 |
| | | 3 | 41,000 |
| | | 4 | — |
| Rat GTR2 (GLUT2) glucose transporter | SEQ ID NO: 4 | 1 | 2,000 |
| | | 2 | 2,000 |
| | | 3 | — |
| | | 4 | — |
| | | 5 | — |
| | | 6 | 7,000 |
| | | 7 | 7,000 |
| | | 8 | 4,000 |
| Rat CFTR chloride transporter | SEQ ID NO: 5 | 1 | 40,000 |
| | | 2 | 40,000 |
| | | 3 | 26,000 |
| | | 4 | 3,000 |
| | | 5 | — |
| | | 6 | — |
| | | 7 | 2000 |
| | | 8 | — |
| Rat CNT2 nucleoside transporter | SEQ ID NO: 6 | 1 | 20,000 |
| | | 2 | 3,500 |
| | | 3 | 19,000 |
| | | 4 | 60,000 |
| | | 5 | — |
| | | 6 | 2,000 |
| | | 7 | 1,500 |
| | | 8 | 2,000 |
| | | 9 | 2,000 |
| | | 10 | 2,000 |
| | | 11 | 32,000 |
| | | 12 | 15,000 |
| Rat MDR1 multidrug resistance transporter | SEQ ID NO: 8 | 1 | 1,000 |
| | | 2 | 18,000 |
| | | 3 | 77,000 |
| | | 4 | — |
| Mouse MDR1 multidrug resistance transporter | SEQ ID NO: 9 | 1 | 12,000 |
| | | 2 | 12,000 |
| | | 3 | 4,000 |
| | | 4 | 4,000 |
| Rat sucrase-isomaltase | SEQ ID NO: 10 | 1 | 3,000 |
| | | 2 | 7,000 |
| | | 3 | 7,000 |
| | | 4 | 2,000 |
| Mouse GLUT7 glucose transporter | SEQ ID NO: 11 | 1 | 4,000 |
| | | 2 | 2,000 |
| | | 3 | 1,000 |
| | | 4 | 2,000 |
| | | 5 | — |
| | | 6 | — |
| | | 7 | — |
| | | 8 | — |
| Rat GCC (guanylyl cyclase) | SEQ ID NO: 27 | 1 | 2,500 |
| | | 2 | — |
| | | 3 | 2,000 |
| | | 4 | — |
| | | 5 | 2,000 |
| | | 6 | 2,000 |
| | | 7 | 6,000 |
| | | 8 | 2,000 |

TABLE 8-continued

ELISA results showing that mouse polyclonal antibodies against the specified RSPEs have been generated.

| SOURCE PROTEIN | Immunising RSPE | Mouse serum sample | 50% Binding Titre (fold dilution) |
|---|---|---|---|
| Rat PLB (phospholipase B) | SEQ ID NO: 28 | 1 | 1,500 |
| | | 2 | — |
| | | 3 | 1,000 |
| | | 4 | — |
| | | 5 | — |
| | | 6 | — |
| | | 7 | — |
| | | 8 | — |
| Rat LPH (lactase-phlorizin hydrolase) | SEQ ID NO: 29 | 1 | 1,500 |
| | | 2 | 3,000 |
| | | 3 | 3,000 |
| | | 4 | 12,000 |
| | | 5 | 15,000 |
| | | 6 | 15,000 |
| | | 7 | 15,000 |
| | | 8 | 15,000 |

4.2.3 Monoclonal Antibodies to an RSPE from the Rat Oligopeptide Transporter PepT1

40 ml of culture supernatant from each of the seven positive monoclonal cell lines producing antibodies against the RSPE having SEQ ID NO 1 (see Example 2.3 above) was affinity purified as described in Example 3.2, and then tested by ELISA as described in Example 4.1 above. Purified monoclonal antibodies were assayed by titration against the immunising peptide (SEQ ID NO: 1). The immune response was assessed by calculating 50% binding titre values (dilution required to reduce maximum signal to 50%). The results are summarised in Table 9 below.

TABLE 9

ELISA results for affinity purified culture supernatant from hybridoma cell lines generated from mice immunised with an RSPE from the Rat oligopeptide transporter PepT1.

| Hybridoma Cell Line | Elution Volume (ml) | Concentration (mg/ml) | 50% Binding Titre (fold dilution) |
|---|---|---|---|
| 1645.142.002 | 3 | 1.4 | 300,000 |
| 1644.112.040 | 4 | 1.1 | 12,500 |
| 1645.451.209 | 2 | 0.1 | — |
| 1647.372.245 | 3 | 1.2 | 92,000 |
| 1646.461.144 | 2 | 0.08 | — |
| 1647.449.047 | 2 | 0.09 | — |
| 1646.240.206 | 2 | 0.1 | — |

Hybridoma cell lines 1645.142.002, 1644.112.040 and 1647.372.245 clearly produce monoclonal antibodies which recognise the RSPE having the sequence of SEQ ID NO 1, which is derived from Rat PepT1.

4.2.4 Monoclonal Antibodies to a RSPE from the Mouse GLUT7 Transporter 40 ml of culture supernatant from each of the four positive monoclonal cell lines producing antibodies against the RSPE having SEQ ID NO 11 (see Example 2.3 above) was affinity purified as described in Example 3.2, and then tested by ELISA as described in Example 4.1 above. Purified monoclonal antibodies were assayed by titration against the immunising peptide (SEQ ID NO: 11). The immune response was assessed by calculating 50% binding titre values (dilution required to reduce maximum signal to 50%). The results for two out of the four anti-GLUT7 monoclonal antibodies are summarised in Table 10 below.

TABLE 10

ELISA results for affinity purified culture supernatant from hybridoma cell lines generated from mice immunised with an RSPE from the Mouse GLUT7 transporter.

| Hybridoma Cell Line | Elution Volume (ml) | Concentration (mg/ml) | 50% Binding Titre (fold dilution) |
|---|---|---|---|
| 1657.183.245.233 | 2.5 | 0.86 | 1,500 |
| 1657.120.223.282 | 2.75 | 0.59 | 4,000 |

4.3 Immunohistochemistry of Rodent Gut Tissue Sections

Rat gut tissue was snap frozen in liquid nitrogen and stored at −80° C. until use. All tissue was sectioned on a cryostat at −20° C. and tissue was placed onto positively charged slides, fixed in ice cold acetone for 10 min and left to air dry. Slides were stored at −20° C. and used within 1 month of sectioning. Prior to starting immunohistochemistry, all slides were allowed to warm up to room temperature. They were then loaded onto the Sequenza, for manual IHC to be performed. All slides were blocked for endogenous peroxidases by application of peroxidase block (provided in Dako Envision® kit) for 6 min at room temperature. The slides were then washed in TRIS-buffered saline (10 mM) with tween 20 (0.1%) (TBST) for 5 min. Non-specific proteins were blocked by addition of 5% milk proteins (Marvel™) for 30 min at room temperature. Slides were washed for 5 min in TBST. Primary antibody (made up in TBST with 1% Marvel™, at dilutions stated in table) was applied and slides were incubated for 1 hour at room temperature. Slides were then washed in TBST (2×5 min). Envision® rabbit polymer was applied and incubated on slides for 30 min at room temperature. Slides were washed (2×5 min) in TBST. DAB was applied for 5 min at room temperature. Slides were washed in distilled $H_2O$, dehydrated through graded alcohols and xylene and then mounted in DPX.

TABLE 11

Summary of immunohistochemistry data for rabbit polyclonal antibodies raised against specific RSPEs

| SEQ ID NO of RPSE against which antibody was raised | Source Protein | Dilution range | Dilution of antibody where staining present | Rat Duodenum | Rat Jejunum | Rat Ileum | Rat Colon | Blocked with blocking peptide |
|---|---|---|---|---|---|---|---|---|
| 1 | Rat oligopeptide transporter PepT1 | 1:20-1:200 | 1:50 | Villi epithelial cells (inconsistent) staining | Villi epithelial cells (inconsistent) staining | No staining | Villi epithelial cells (inconsistent) staining | Blocking data inconclusive |
| 2 | Rat oligopeptide transporter PepT1 | 1:10-1:200 | | No staining | No staining | | | |
| 3 | Rat CD155 (PVR, Tage4) | 1:10-1:200 | | Lamina propria staining (non-specific) | Lamina propria staining (non-specific) | | | |
| 4 | Rat GTR2 (GLUT2) glucose transporter | 1:10-1:200 | 1:10 | Crypt epithelial cells, patchy villi epithelial cells staining | Crypt epithelial cells staining | Crypt epithelial cells staining | Crypt epithelial cells staining | |
| 5 | Rat CFTR chloride transporter | 1:25-1:200 | 1:50 | Villi epithelial cells and crypt epithelial cells staining | Crypt epithelial cells staining | Crypt epithelial cells staining | Villi epithelial cells and crypt epithelial cells staining | Staining was successfully blocked with excess peptide |
| 6 | Rat CNT2 nucleoside transporter | 1:25-1:200 | 1:50 | Muscularis mucosa staining and villi and crypt epithelial cells staining | Muscularis mucosa staining | Muscularis mucosa staining and villi and crypt epithelial cells staining | Muscularis mucosa staining and villi and crypt epithelial cells staining | Staining was successfully blocked with excess peptide |
| 8 | Rat MDR1 multidrug resistance transporter | 1:10-1:200 | | No staining | No staining | | | |
| 9 | Mouse MDR1 multidrug resistance transporter | 1:10-1:200 | | No staining | No staining | | | |
| 10 | Rat sucrase-isomaltase | 1:10-1:200 | | No staining | No staining | | | |
| 11 | Mouse GLUT7 glucose transporter | 1:25-1:200 | 1:50 | Staining on Brunners Glands | Crypt epithelial cells staining | Crypt epithelial cells staining | Crypt epithelial cells staining | Staining was successfully blocked with excess peptide |
| 12 | Mouse GLUT7/Rat GTR5 (GLUT5) glucose transporters | 1:10-1:200 | | No staining | No staining | | | |
| 15 | Rat OATP-B (SLC21A9) organic anion transporting polypeptide | 1:10-1:200 | | Possible crypt epithelial staining | | | | |
| 27 | Rat GCC (guanylyl cyclase) | 1:25-1:200 | 1:25 | Crypt epithelial cells and villi epithelial cells staining | Crypt epithelial cells and villi epithelial cells staining | Crypt epithelial cells and villi epithelial cells staining | Crypt epithelial cells and villi epithelial cells staining | Staining was successfully blocked with excess peptide |
| 28 | Rat PLB (Phospholipase B) | 1:25-1:200 | 1:50 | Villi and crypt epithelial cells staining | Villi and crypt epithelial cells staining | Villi and crypt epithelial cells staining | Villi and crypt epithelial cells staining | Staining was not successfully blocked with excess peptide - indicating non-specific staining seen |
| 29 | Rat LPH (lactase-phlorizin hydrolase) | 1:25-1:200 | 1:25 | Possible crypt and villi epithelial cells staining | Possible crypt and villi epithelial cells staining | No staining | No staining | Staining in duodenum and jejunum successfully blocked with excess peptide |
| 31 | Rat AMPN (aminopeptidase N) | 1:25-1:200 | | No staining | No staining | No staining | No staining | |

TABLE 11-continued

Summary of immunohistochemistry data for rabbit polyclonal antibodies raised against specific RSPEs

| SEQ ID NO of RPSE against which anti-body was raised | Source Protein | Dilution range | Dilution of anti-body where staining present | Rat Duodenum | Rat Jejunum | Rat Ileum | Rat Colon | Blocked with blocking peptide |
|---|---|---|---|---|---|---|---|---|
| 32 | Rat MCDL (mucin and cadherin-like protein) | 1:25-1:200 | | No staining | No staining | No staining | No staining | |
| 34 | Rat SCAB (amiloride-sensitive sodium channel beta-subunit) | 1:25-1:200 | | No staining | No staining | No staining | No staining | |

Specific staining was assessed with the use of blocking peptides. Primary antibodies, at the dilution to give optimum staining, were incubated with a 10 fold excess of peptide for 2 hours at room temperature in TBS with 1% Marvel™, before application onto the slides the remaining protocol was as described above. The results are summarised in Table 11 above.

Example 5

Production of Recombinant Protein Toxins

5.1 Recombinant Gelonin Production

The gene encoding the 251 amino acid gelonin protein (see Nolan et al., 1993, Gene 134: 223-227) together with the pelB leader sequence and a C-terminal hexa-histidine tag were codon optimised for *E. coli* expression and cloned into an *E. coli* expression vector (pDGF—derived from the NEB vector pMALc-2, pDGF contains all of the features of pMALc-2 except for the sequence encoding the maltose binding protein, which has been excised) under the control of the hybrid tac promoter. The recombinant vector was transformed into *E. coli* strain TOP10.

Expression of gelonin was achieved by growing the transformed TOP10 cells in LB medium with induction at 28° C. with 1 mM IPTG for 20 hours. Following harvesting of *E. coli* cells the cells were disrupted using a French pressure cell (Constant Systems; disruption at 20,000 psi) in 1×PBS/30 mM Imidazole. The soluble extract was applied to a GraviTrap column (GE Healthcare) and after a 15 ml wash with 1×PBS/30 mM Imidazole, gelonin was eluted in 1×PBS/500 mM Imidazole. As a second purification step, the eluate was desalted into 20 mM sodium phosphate buffer pH 8.0 and applied to a Resource S cation exchange column with a 0 to 1M salt gradient elution.

To determine whether the recombinant gelonin was active (functional) the purified gelonin protein was tested in a protein translation inhibition assay (TNT T7 quick coupled transcription/translation system, Promega) using T7 luciferase DNA as the substrate. As a positive control, cycloheximide was used. This demonstrated that the recombinant purified gelonin inhibited translation of the T7 luciferase DNA.

5.2 Recombinant VIP2A Production

The gene encoding the 464 amino acid VIP2A protein (see U.S. Pat. No. 5,849,870) together with a C-terminal hexa-histidine tag was codon optimised for *E. coli* expression and cloned into the pET24a expression vector (Novagen). The recombinant vector was transformed into *E. coli* strain BL21 (DE3).

Expression of VIP2A was achieved by growing the transformed BL21(DE3) cells in LB medium with induction at 28° C. with 1 mM IPTG for 20 hours. Following harvesting, the cells were disrupted using a French pressure cell as described in Example 5.1 above. The soluble extract was applied to a HisTrapHP column (GE Healthcare) and after washing with 5 column volumes of PBS/20 mM imidazole, VIP2A protein was eluted with a gradient of up to 500 mM imidazole.

SDS-PAGE analysis of the soluble extract and sample from the purification revealed a band at the expected size for recombinantly produced Histidine-tagged VIP2A.

5.3 Expression Construct for the Production of Recombinant Granzyme B

A gene encoding the 228 amino acid mature Granzyme B protein from rat (see Genbank accession No M34097 for sequence information) was artificially synthesised (DNA fragment 050031) and cloned into pCR-Script to give plasmid p050031. A nested PCR approach was taken to introduce the Granzyme B coding sequence into the expression vector pET32a(+) (Novagen).

The mature Granzyme B coding sequence from p050031 was PCR amplified using primers RoPro070 petEK/rGrzB F1 (SEQ ID NO: 51) and RoPro067 rGrzB R (SEQ ID NO: 52) to introduce a 5' tail homologous to the enterokinase site present in the fusion tag in pET32a(+). The resulting PCR product was used as a template for the second part of the nested PCR, which was carried out using primers RoPro076 petEK/rGrzB F2 (SEQ ID NO: 53) and RoPro067rGrzB R (SEQ ID NO: 52) to introduce a 5' KpnI site.

The final PCR product was digested with KpnI/NotI and ligated into similarly digested pET32a(+) to give expression vector pET32a(+)::rGrzB. This results in a clean fusion between the N-terminal expression tag from the host vector and recombinant Granzyme B coding sequence, thus permitting activation of recombinant Granzyme B by treatment with enterokinase following expression. The final expression vector pET32a(+)::rGrzB may be transformed into any suitable *E. coli* expression host (e.g. RosettaGami (DE3)).

The sequences of the primers used in the construction of pET32a(+)::rGrzB are as follows (all primer sequences are given 5' to 3'): RoPro070 petEK/rGrzB F1 (SEQ ID NO: 51) GGTACCGACGACGACGACAAGATCATCG-GTGGTCACGAAGCT AAGCCAC; RoPro067 rGrzB R (SEQ ID NO: 52) AGCTGGCGGCCGCCTAGGAC; RoPro076 petEK/rGrzB F2 (SEQ ID NO: 53) AGATCTGGGTACCGACGACGACGA C.

Example 6

Conjugation of Antibody Components to Toxins 6.1 Conjugation of Commercially Available Gelonin to Polyclonal Anti-Rat CNT2 Antibodies The strategy chosen to carry out this procedure is to activate the antibody with the cross linker SPDP (N-succinimidyl 3-[2-pyridyldithio]propionate; Pierce Chemical Co.) which will form disulphide link to thiolated toxin. The method used came from; Hermanson 1996 "Bioconjugate Techniques" (Academic Press pp. 509) which stated that the conjugation would not interfere with the activity of the toxin gelonin (30 kDa). Both 5:1 and 10:1 molar ratios of gelonin to anti-CNT2 polyclonal antibody were used to obtain the most efficient reaction mix.

6.1.1 SPDP Treatment of CNT2 Polyclonal Antibody

A 1 ml aliquot of the protein A purified rabbit 1 polyclonal IgG (see Example 4.2.1, harvest bleed from rabbit 1 was affinity purified and then purified using a Protein A column) was concentrated using a centricon spin concentrator with 10 kDa cut off. The resulting 160 ul was made up to a 10 mg/ml solution in PBS 10 mM EDTA pH 8. 6 ul SPDP (3 mg/ml in DMF) was added to 200 ul of antibody solution and incubated for 30 mins at room temperature. The reaction mixture was applied to a PD10 desalting column equilibrated with PBS+10 mM EDTA pH 8. All of the 3.5 ml sample volume was collected and concentrated using a centricon concentrator to obtain SPDP-treated anti-CNT2 antibody at a final concentration of 3.6 mg/ml.

6.1.2 Thiolation of Gelonin

Gelonin was obtained from Aczon SpA as a 5 mg sample of lyophilised protein purified from the seeds of *Gelonium multiflorum*. The sample was originally dissolved in PBS at a concentration of 5 mg/ml. 300 ul of this solution was concentrated in a centricon concentrator and the volume reduced to 55 ul. This was then diluted in 50 mM triethanolamine 10 mM EDTA pH 8 to give a 10 mg/ml gelonin solution. 2-Immunothiolane was dissolved to give a 20 mg/ml solution in distilled water. 10.5 ul of 2-immunothiolane solution this was added to 150 ul gelonin solution and the mixture incubated on ice for a hour. The activated gelonin was applied to a PD10 desalting column equilibrated with PBS+10 mM EDTA pH 8. All of the 3.5 ml sample volume was collected and concentrated in a centricon concentrator to obtain thiolated gelonin at a final concentration of 3 mg/ml.

6.1.3 Conjugation of Anti-CNT2 Polyclonal Antibody to Gelonin

To obtain a 5:1 molar ratio of gelonin to anti-CNT2 antibody, 0.5 mg thiolated gelonin needed to be reacted with 0.5 mg anti-CNT2 antibody. Accordingly, 138 ul of SPDP treated anti-CNT2 antibody was added to 167 ul of thiolated gelonin.

The reaction was also carried out at a 10:1 molar ratio of gelonin to anti-CNT2 antibody (1 mg thiolated gelonin in 333 ul was added to 0.5 mg SPDP-treated anti-CNT2 antibody in 138 ul). Each reaction was sealed under nitrogen and incubated for 20 hours at 4° C. After this time any unreacted sulfhydryl residues were blocked by the addition of iodoacetamide to a final concentration of 2 mM.

6.1.4 Analysis of Conjugate

Each reaction mixture was analysed by MALDI-TOF mass spectrometry, SDS-PAGE and ELISA. Data (not shown) obtained from SDS-PAGE separation of the reaction mixtures and mass spectrometry revealed show that each conjugation reaction was successful, and species were identified with 1, 2 and 3 molecules of gelonin conjugated to a single antibody molecule. Although mass spectrometry data revealed the presence of some unconjugated antibody, the amount was insufficient to be observed on a coomassie stained SDS-PAGE gel. There appeared to be no difference in efficiency of conjugation between the 2 reaction ratios.

ELISA assays were carried out as described previously on each reaction mixture in order to assess whether the binding activity of the antibody was affected by the conjugation reaction. The data obtained is summarised in Table 12 below.

TABLE 12

ELISA data for conjugation of gelonin to anti-CNT2 polyclonal antibodies

| Sample | 50% Binding Titre |
|---|---|
| Anti-CNT2 polyclonal | 0.051 ug/ml |
| SPDP-treated anti-CNT2 polyclonal | 0.134 ug/ml |
| 5:1 molar ratio thiolated gelonin:SPDP treated anti-CNT2 polyclonal | 0.33 ug/ml |
| 10:1 molar ratio thiolated gelonin:SPDP treated anti-CNT2 polyclonal | 0.22 ug/ml |

It can be that the binding has been affected by both the addition of the SPDP polylinker and by the conjugation to gelonin. However, the conjugated antibody reaction mixture still exhibits significant binding. This can be attributed to both conjugated and non-conjugated antibody in the reaction mixture. Since the amount of unconjugated antibody is low, it is assumed that a good proportion of the binding observed may be attributed to the conjugated antibody.

6.2 Conjugation of Recombinant Gelonin to Polyclonal Anti-Rat CNT2 Antibodies

The same strategy as outlined above in Example 6.1 was adopted in order to conjugate recombinant gelonin, produced as described in Example 5 above, to polyclonal anti-Rat CNT2 antibodies. A 5:1 gelonin to anti-CNT2 polyclonal antibody molar ratio was used to obtain the most efficient reaction mix.

6.2.1 SPDP Treatment of Anti-CNT2 Polyclonal Antibody 3.75 mg of the protein A purified rabbit 1 polyclonal as a 10 mg/ml solution in PBS/10 mM EDTA pH 8 was mixed with 11.25 ul SPDP (3 mg/ml in DMF) and incubated for 30 mins at room temperature. The reaction mixture was passed through a Zeba (Pierce Chemical Co.) desalting column pre-equilibrated with PBS/10 mM EDTA pH 8.

6.2.2 Thiolation of Recombinant Gelonin 3.75 mg of recombinant gelonin was made up to 10 mg/ml in 50 mM triethanolamine 10 mM EDTA pH 8. 2-Iminothiolane (Traut's reagent; Sigma-Aldrich) was dissolved to 20 mg/ml in de-gassed and nitrogen-bubbled deionised $H_2O$, 26.25 ul of this was added to the gelonin solution and incubated in a nitrogen atmosphere on ice for one hour. The thiolated gelonin was passed through a Zeba (Pierce Chemical Co.) desalting column pre-equilibrated with PBS/10 mM EDTA pH 8.

6.2.3 Conjugation of Anti-CNT2 Polyclonal Antibody to Recombinant Gelonin

The SPDP-reacted antibody solution was mixed with the thiolated recombinant gelonin solution resulting in equal quantities of each protein constituent, providing a 5:1 molar ratio of recombinant gelonin to antibody. The reaction was sealed under nitrogen and incubated for 20 hours at 4° C.

After this time any unreacted sulfhydryl groups were blocked by the addition of iodoacetamide to a final concentration of 2 mM, followed by a minimum of one hours incubation at room temperature.

6.2.4 Separation of the Conjugate from Unconjugated Recombinant Gelonin

Gel-filtration with PBS was used to separate unconjugated gelonin molecules from conjugates. A 10/300 Superdex 200 column (Amersham-Pharmacia) was equilibrated in PBS for 3 column volumes (CVs) using an Akta FPLC unit (Amersham-Pharmacia). Chromatography was controlled by a PC running Unicorn software (Amersham-Pharmacia), which injected the sample and then maintained a 0.5 ml/min flow rate, with 0.5 ml fractions collected into a 96 well block after 0.1 CVs had eluted. Elution was allowed to proceed for 1.4 CVs.

Selected fractions were analysed on a non-reducing SDS-PAGE gel (4-12% bis-tris NuPage in MOPS buffer; Invitrogen) as described by the manufacturer. The gel was stained using the SimplyBlue coomassie stain (Invitrogen) as described by the manufacturer. The fractions that were determined to contain the conjugates were pooled and submitted to the next step of purification.

6.2.5 Separation of the Conjugate from Unconjugated Anti-CNT2 Antibody

The presence of a hexa-histidine C-terminal tail on the recombinant gelonin molecules allowed the application of immobilised metal-chelate affinity chromatography (IMAC) as a second chromatographic step in the purification of the conjugates. The lack of a hexa-histidine motif on the unconjugated antibody (still present in the conjugate fractions after gel-filtration) allows the removal of free antibody from hexa-histidine containing conjugates. Therefore, the pooled fractions obtained in 6.2.4 above were passed through a HisTrap HP 1 ml nickel-affinity column (pre-equilibrated by 5 CVs of PBS/15 mM imidazole; Amersham Biosciences) attached to an Akta FPLC unit controlled by a PC running Unicorn software (Amersham Biosciences). Loading and washing of the column was carried out over 5 CVs using PBS/15 mM imidazole as the load/wash buffer. Elution of hexa-histidine containing proteins was effected by the application of a gradient of 15 mM to 500 mM imidazole (in PBS) over 20 CVs. Fractions were collected in 0.5 ml volumes in a 96 well block.

Selected fractions were analysed on a non-reducing SDS-PAGE gel (4-12% bis-tris NuPage in MOPS buffer; Invitrogen) as described by the manufacturer. The gel was stained using the SimplyBlue™ coomassie stain (Invitrogen) as described by the manufacturer.

The gel revealed that the conjugates were substantially purified away from free antibody by the IMAC step. Fractions containing the conjugates were pooled and desalted into PBS using VivaSpin 20 ml spin concentrators with a 10 kD molecular weight cut-off.

6.2.6 Analysis of Conjugate

MALDI-TOF mass-spectrometry was used to analyse the composition of the pooled conjugate sample relative to unconjugated anti-CNT2 antibody. The mass spectra obtained (not shown), indicated the presence of 1:1, 1:2 and 1:3 ratio's of antibody:gelonin conjugate species in the pooled conjugate fraction (Pool B). No singly charged unconjugated antibody species was observed, however a peak on the spectrum was identified which correlates with a doubly-charged species of unconjugated antibody. Thus, even though the majority of the unconjugated antibody was purified away from conjugated antibody (as indicated by SDS-PAGE analysis of the IMAC purification), it may be inferred that a very small amount of unconjugated antibody remains in the pooled purified sample.

The functional activity of the conjugate in the MAC-purified pooled sample was assessed by ELISA (to determine the affect of conjugation on antibody binding) and by an in vitro translation inhibition assay (to determine whether the functional activity of gelonin had been affected by conjugation).

The ELISA (data not shown) revealed similar results to those observed for conjugation to commercially supplied gelonin (Example 6.1.4 above): antibody binding was affected by both the addition of the SPDP polylinker and by the conjugation to recombinant gelonin, but the conjugated antibody reaction mixture still exhibited significant binding to the Rat CNT2 RSPE. Although the mass-spectrometry analysis indicated that there may still be some unconjugated antibody remaining even after the IMAC purification, the amount of unconjugated antibody in the MAC purified samples will be less than in the conjugation reaction mixture for the natural gelonin/anti-CNT2 antibody as a consequence of the IMAC purification. Accordingly, the antibody binding observed may be attributed as being mainly due to anti-CNT2 antibody-recombinant gelonin conjugate.

Figure 2:
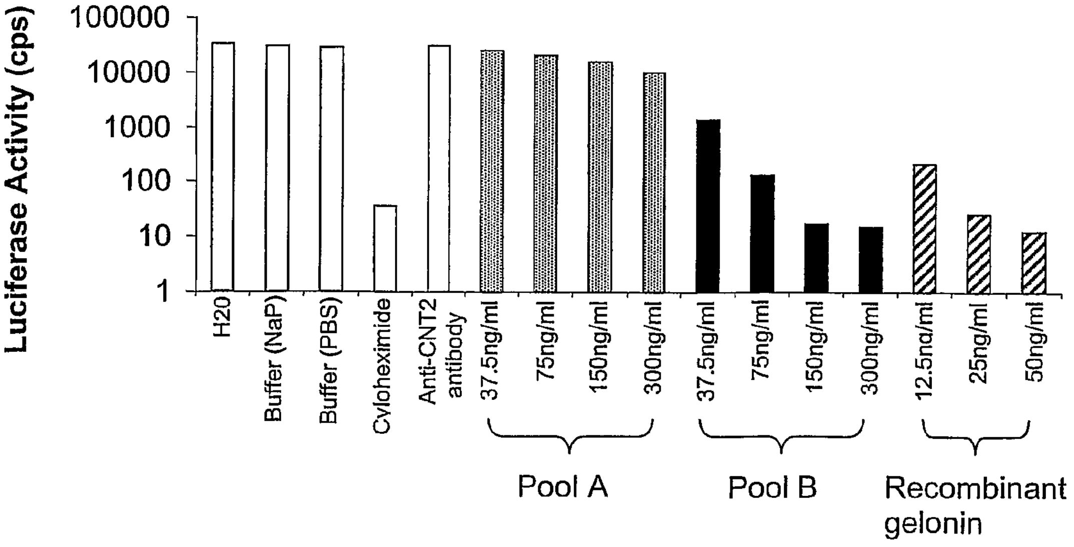
FIG. 2 Inhibition of luciferase translation by anti-CNT2 polyclonal antibody-recombinant gelonin conjugate. Pool A samples correspond to the pooled fraction from the IMAC purification which were determined to contain free antibody. Pool B samples correspond to the pooled fractions from the IMAC purification which were determined to contain antibody-toxin conjugate.

The retention of ribosome-inhibiting capability of the recombinant gelonin conjugated to the anti-CNT2 antibody in the pooled conjugate containing sample from the IMAC purification was determined using the TNT quick coupled transcription/translation system (Promega) as described by the manufacturer. FIG. 2 shows the results. The translational inhibition exhibited by conjugates in IMAC purified pooled sample (Pool B) is equivalent to that of the original recombinant gelonin (rGelonin). Thus ribosome-inhibitory capability has been maintained following conjugation.

6.3 Conjugation of Commercially Available β-purothionin to Polyclonal Anti-Rat CNT2 Antibodies The strategy chosen for this conjugation was to use the TFCS cross linker (Pierce), which has a large spacer arm, in order to give as much exposure as possible to the relatively small (5 kDa) β-purothionin molecule. TFCS has a NHS ester group at one end, which binds to amine groups on the antibody, and a protected amine group at the other end, which is exposed for reacting to appropriately treated β-purothionin by raising the pH to 8. Carboxyl groups on the purothionin are reacted with EDC to form an unstable amine reactive intermediate which is then reacted with sulfo-NHS to provide a more stable linkage. The EDC/sulfo-NHS treated β-purothionin is then bound to the amine end of the TFCS linker.

6.3.1 TFCS Treatment of CNT2 Polyclonal

A 1 ml aliquot Protein A purified rabbit 1 polyclonal IgG (see Example 4.2.1, harvest bleed from rabbit 1 was affinity purified and then purified using a Protein A column) was concentrated using a centricon spin concentrator with 10 kDa cut off. The resulting sample volume was up to 5 mg/ml 0.1M Sodium Phosphate buffer 0.15M NaCl pH 7.2. 15 ul TFCS (3 mg/ml in DMF) was added per 500 μl of antibody and incubated for 1 hour at room temperature. The reaction mixture was applied to a PD10 desalting column equilibrated with 0.1M phosphate buffer pH 8. All of the 3.5 ml sample volume was collected and concentrated using a centricon concentrator to obtain TFCS-treated anti-CNT2 antibody at a final concentration of 10 mg/ml.

6.3.2 EDC and Sulfo-NHS Treatment of β-purothionin

Lyophilised β-purothionin from wheat endosperm (Takara) was dissolved in 0.1M Sodium Phosphate buffer 0.15M NaCl pH 7.2 to final concentration of 10 mg/ml. EDC was added to give a final concentration 2 mM along with sulfo-NHS to a final concentration of 5 mM, and the mixture was left to react at room temperature for 15 minutes. The reaction was stopped by adding 2-mercaptoethanol to a final concentration of 20 mM. The activated β-purothionin was applied to a polyacrylamide desalting column (size exclusion limit of 1,800 Da; Pierce) equilibrated with 0.1M Sodium Phosphate buffer, 0.15M NaCl pH 7.2. Fractions were collected and the OD280 nm checked for the presence of the toxin.

6.3.3 Conjugation of Anti-CNT2 Polyclonal Antibody to Activated β-purothionin

TFCS-treated antibody and EDC/sulfo-NHS treated β-purothionin were mixed to give a 30:1 molar ratio of β-purothionin:anti-CNT2 antibody and left to react at 4° C. overnight. The reaction was then stopped by adding hydroxylamine to a final concentration 10 mM. The reaction mixture was then applied to a size exclusion chromatography column to separate free β-purothionin from antibody-β-purothionin conjugate. Fractions containing the conjugate were pooled.

6.3.4 Analysis of Conjugate

MALDI-TOF mass-spectrometry was sued to analyse the composition of the pooled conjugate sample relative to unconjugated anti-CNT2 antibody. The mass spectra obtained (not shown) indicated the presence of 1:1, 1:2 and 1:3 ratios of antibody-β-purothionin conjugate species in the pooled conjugate fractions. Some singly charged unconjugated antibody species was also observed.

The functional activity of the conjugate in the pooled sample was assessed by ELISA as described previously. The 50% binding titre for the conjugate was calculated at 0.067 μg/ml in comparison to 0.041 μg/ml for unconjugated anti-CNT2 antibody.

TABLE 13

Immunohistochemical analysis of rat gastro-intestinal tissue with anti-CNT2::β-purothionin conjugate

| Dilution range | Dilution of conjugate with staining present | Rat Duodenum | Rat Jejunum | Rat Ileum | Rat Colon | Blocked with blocking peptide |
|---|---|---|---|---|---|---|
| 1:25-1:50 | 1:25 & 1:50 | Muscularis mucosa staining and villi and crypt epithelial cells staining | Not tested | Not tested | Muscularis mucosa staining and villi and crypt epithelial cells staining | Not tested |

A sample of the anti-CNT2::β-purothionin conjugate was used for immunohistochemical analysis of rodent gastro-intestinal tissue (see Example 4.2 for methodology). The results are summarised in Table 13 above.

Example 7

Fusion Protein Expression Vector Construction

Fusion protein expression vectors were constructed between a scFv recognising a cell-surface antigen and three different protein toxins, gelonin, granzyme B, and cyt2A. The scFvs used in this exemplification are the SV63 scFvs described in Example 2.5 above. Standard molecular biology techniques for plasmid preparation, restriction enzyme digestion, ligation, *E. coli* transformation etc were followed throughout.

7.1 Gelonin-scFv Fusion Constructs

The gene encoding the 251 amino acid gelonin protein (see Nolan et al. supra) was synthesised artificially with the 5' sequence designed to permit in-frame fusion to either the $V_H$ (giving rise to artificial gene 054014) or $V_L$ (giving rise to artificial gene 054013) encoding sequence from the SV63 antibody, and sub-cloned into pCR-Script to give the two constructs p054013 and p054014.

Plasmid p054013 was digested with SpeI and NotI and the fragment encoding gelonin that was generated was purified and ligated to similarly digested pDGF-SV63-VHVL, to give vector pDGF-SV63-VHVLrGel. This created an in-frame fusion between the N-terminus of the SV63 scFv via a single $Gly_4Ser$ linker to the recombinant Gelonin. Thus the expression cassette in pDGF-SV63-VHVLrGel comprises the following components in the 5' to 3' direction: tac promoter, pelB leader sequence, SV63 $V_H$ coding sequence, $[Gly_4Ser]_3$ linker, SV63 $V_L$ coding sequence, $Gly_4Ser$ linker, recombinant Gelonin encoding sequence.

The SV63 $V_H$ coding sequence, $[Gly_4Ser]_3$ linker, SV63 $V_L$ coding sequence, $Gly_4Ser$ linker, and recombinant Gelonin encoding sequence, can easily be excised as a NcoI/EcoRI fragment and ligated into alternative expression/cloning vectors, for example into pIMS147 or pET32a, if desired.

Plasmid p054014 was digested with BseRI and NotI and the fragment generated encoding gelonin was purified and ligated into similarly digested pDGF-SV63-VLVH, to give vector pDGF-SV63-VHVLrGel. This created an in-frame fusion between N-terminus of the scFv via a single $Gly_4Ser$ linker to the recombinant Gelonin. Thus the expression cassette in pDGF-SV63-VHVLrGel comprises the following components in the 5' to 3' direction::tac promoter, pelB leader sequence, SV63 $V_L$ coding sequence, $[Gly_4Ser]_3$ linker, SV63 $V_H$ coding sequence, $Gly_4Ser$ linker, recombinant Gelonin encoding sequence.

The SV63 $V_L$ coding sequence, $[Gly_4Ser]_3$ linker, SV63 $V_H$ coding sequence, $Gly_4Ser$ linker, and recombinant Gelonin encoding sequence, can easily be excised as a NcoI/EcoRI fragment and ligated into alternative expression/cloning vectors, for example into pIMS147 or pET32a, if desired.

7.2 Granzyme B-scFv Fusion Constructs

Two constructs were made, each carrying Granzyme B fused N-terminal to a SV63 scFv: pET32a::rGrzB::SV63 VHVL and pET32a::rGrzB::SV63 VLVH.

Plasmid pET32a::rGrzB::SV63 VHVL was constructed using pET32a(+)::rGrzB (Example 5.3 above) as a template in conjunction with a primer overlap extension approach to fuse mature GranzymeB coding sequence to the SV63 scFv in the $V_HV_L$ orientation (N to C-terminus) via a single $Gly_4Ser$ linker.

(i) 3' terminal sequence encoding a single $Gly_4Ser$ linker was added to the mature Granzyme B coding sequence by using pET32a(+)::rGrzB as a template for PCR with pET F (SEQ ID NO: 54) and RoPro 071 G4S/rGrzB R1 (SEQ ID NO: 55) primers.

(ii) 5' terminal sequence coding for a single Gly4Ser linker and part of the Granzyme B coding sequence was added to the SV63 VHVL coding sequence, using the pDGF-SV63-VHVL as a template for PCR with RoPro 074 rGrzB/G4S/VHVL F (SEQ ID NO: 56) and RoPro 075 pET/VHVL R (SEQ ID NO: 57) primers.

Products from (i) and (ii) above were purified and mixed in equimolar amounts prior to primer-free extension and subsequent PCR using pET F (SEQ ID NO: 54) and RoPro 075 pET/VHVL R (SEQ ID NO: 57) to amplify a full-length fusion product that was cloned into pET32a(+) using unique SfuI and NotI sites.

Plasmid pET32a::rGrzB::SV63 VLVH was also constructed using pET32a(+)::rGrzB (Example 5.3 above) as a template in conjunction with a primer overlap extension approach to fuse mature GranzymeB coding sequence to the SV63 scFv in the $V_LV_H$ orientation (N to C-terminus) via a single $Gly_4Ser$ linker.

(i) 3' terminal sequence coding for a single $Gly_4Ser$ linker was added to the Granzyme B coding sequence as described in (i) above.

(ii) 5' terminal sequence coding for a single Gly4Ser linker and part of the Granzyme B coding sequence was added to the SV63 VLVH coding sequence, using pDGF-SV63-VLVH as a template for PCR with RoPro 072 rGrzB/G4S/VLVH F (SEQ ID NO: 58 and RoPro 073 VLVH/pET R (SEQ ID NO: 59) primers Products from (i) and (ii) above were purified and mixed in equimolar amounts prior to primer-free extension and subsequent PCR using pET F (SEQ ID NO 54) and RoPro 073 VLVH/pET R (SEQ ID NO: 59) to amplify a full-length fusion product that was subsequently cloned into pET32a(+) using unique SfuI and NotI sites.

The sequences of the primers used in the construction of the Granzyme B-scFv fusion constructs are as described in Example 5.3 above and as follows (all primers given 5' to 3'): pET F (SEQ ID NO: 54) TCGGTGATGTCGGCGATATAG; RoPro 071 G4S/rGrzB R1 (SEQ ID NO: 55) ACTACCTC-CGCCACCGGACTTCTTCATA GTTTTCTTGATC-CAGG; RoPro 074 rGrzB/G4S/VHVL F (SEQ ID NO: 56) GAAGAAGTCCGGTGGCGGAGGTAGTGAG-GTCCAGCTGCAGGAGTCTGG CCCTGG; RoPro 075 pET/VHVL R (SEQ ID NO: 57) TGCTCGAGTGCGGCCG CTTATTACTTGATCTCCAGTTTGGTGC-CTCCACCGAACG; RoPro 072 rGrzB/G4S/VLVH F (SEQ ID NO: 58) GAAGAAGTCCGGTGGCGGAGGTAG TGATATCGTTCTCACTCAATCTCCAGCAATC; RoPro 073 VLVH/pET R (SEQ ID NO: 59) TGCTCGAGTGCG-GCCGCTTATTATGAGGAGACTGTGAGAGTGGTG CCTTGGCC.

7.3 Cyt2A-scFv Fusion Constructs

In order to create in-frame fusions of the SV63 scFv and Cyt2A sequences the example of Gurkan & Ellar (2003 Protein Expr. Purif. 29(1):103-16) was followed. The gene encoding the first 237 amino acids of Cyt2Aa1 (EMBL:BT-CYTBG) was synthesised artificially to contain a 3' sequence designed to create an in-frame C-terminal addition of the 14 amino acid Xpress epitope (Invitrogen). This artificially synthesised Cyt2A-Xpress epitope sequence is known as 051072, and was sub-cloned in to pCR Script to give p051072. The plasmid pDGF-SV63-VHVL (see Example 2.5) was altered in two steps. Firstly, an artificially synthesised sequence was designed and produced (named p054247) that would create a linking fragment by containing part of the 3' terminal sequence of the SV63 VL sequence, the $(Gly_4Ser)_3$ linker and part of the 5' terminal sequence of the mature Cyt2Aa1 protein (as described by Gurkan & Ellar, supra). This fragment was excised from p054247 using SpeI (5') and EcoRI (3'), and ligated into similarly prepared pDGF-SV63-VHVL (see Example 2.5). The resulting plasmid was then further modified by cutting with SfuI and BamHI and introducing the approximately 520 bp SfuI/BamHI fragment (representing the 3' end of the mature Cyt2Aa1 sequence plus the Xpress epitope) from p051072. The resulting plasmid (pDGF-SV63-VHVL::Cyt2A) comprises a complete in-frame fusion of the SV63 $V_HV_L$ scFv via a flexible linker to the active (mature) form of Cyt2Aa1 (amino acids 37 to 237) followed by the Xpress epitope.

Similarly, the plasmid pDGF-SV63-VLVH was modified in a two-step process to introduce the Cyt2Aa1 sequence. Firstly, an artificially synthesised sequence was designed and produced (named 054248) that would create a linking fragment by containing part of the 3' terminal sequence of the SV63 VH sequence, the $(Gly_4Ser)_3$ linker and part of the 5' terminal sequence of the mature Cyt2Aa1 protein (as described by Gurkan & Ellar, supra). The artificial sequence was sub-cloned into pCR Script to give plasmid p05428. This fragment was then excised from p054248 using BseRI (5') and EcoRI (3'), and ligated into similarly prepared pDGF-SV63-VLVH. The resulting plasmid was then further modified by cutting with SfuI and BamHI and introducing the approximately 520 bp SfuI/BamHI fragment (representing the 3' end of the mature Cyt2Aa1 sequence plus the Xpress epitope) from p051072. The resulting plasmid (pDGF-SV63-VLVH::Cyt2A) comprises a complete in-frame fusion of the SV63 $V_LV_H$ scFv via a flexible linker to the active (mature) form of Cyt2Aa1 (amino acids 37 to 237) followed by the Xpress epitope

Example 8

Expression of Fusion Proteins

The vectors carrying the SV63 scFv-gelonin fusion genes (see Example 7.1 above) were transformed into *E. coli* TOP10 cells. Pilot expression studies were performed by growing the transformed cells in 2×YT/2% glucose medium, before inducing at either 20° C. or 15° C. in 2×YT medium supplemented with 1 mM IPTG for 16 hours. Small samples (10 mls) were harvested and centrifuged and each cell pellet was resuspended in 1 ml lysis buffer (PBS). The samples were sonicated, re-centrifuged at 13,000 rpm for 5 minutes at room temperature, and the supernatants (soluble fractions) decanted. The pellets (insoluble fractions) were resuspended in 1 ml lysis buffer.

Soluble and insoluble fractions were analysed by Western blot using an antibody directed to the hexa-histidine tag. The analysis revealed that scFv-gelonin fusion protein was being produced from both expression vectors (i.e. where the scFv was in the $V_HV_L$ orientation and where the scFv was in the $V_LV_H$ orientation). However, the $V_LV_H$ orientation of the scFv gave a higher yield of soluble protein.

Larger scale growth and induction was carried out, and scFv-gelonin fusion protein was further purified from the soluble fraction through purification on a Gravitrap column.

Example 9

In Vitro Testing of Protein Conjugates and Fusion Proteins

The ability of protein conjugates and fusion proteins of the invention to cause damage to the upper gastrointestinal tract is assessed by measuring the permeability of the mucosa to the non-absorbable marker, mannitol, using sections of isolated rat duodenum. Tissues isolated in vitro are exposed to these rodent control agents, using a modification of a method published previously (Heylings, 1991, Toxicol. Appl. Pharmacol. 107:482-493).

Briefly, a 10 cm section of gastrointestinal tract (immediately distal to the stomach) from adult male Alderley Park strain rats (Ap:Ak$_f$SD) is removed immediately after humane termination. The tissue is placed in oxygenated TC199 media and any food debris is carefully flushed out of the gut using TC199 media from the end furthest away from the stomach. Two sections of duodenum are prepared, each 2.5 cm in length, the proximal section (immediately after the stomach) and the distal section (immediately after entrance of the bile duct).

The sections are carefully attached taut by means of ligatures to the open ends of two glass tubes connected to a reservoir. This allows the luminal (mucosal) and blood-side (serosal) surfaces of the isolated musosa to be bathed by separate solutions. The gap between the ends of the glass rods in each mucosal chamber is 12 mm. A diagrammatic representation of the apparatus is similar to that shown in the upper part FIG. 1 from Heylings 1991 supra. The chamber with mucosa attached is rinsed with oxygenated TC199 media several times to remove excess mucus on the luminal side of the tissue. The luminal (mucosal) side is filled with 4 ml of TC199 media containing 20 mg mannitol/ml (TC199-M), and the mucosa is checked for leakage. The mucosal chamber is immersed in an outer cup-shaped glass vessel filled with 40 ml TC199 media (serosal side solution) which is gassed with 95% $O_2$:5% $CO_2$. The chamber is positioned to avoid hydrostatic pressure gradients between the two bathing solutions. Both solutions are maintained at 37±0.1° C. by means of a water jacket connected to an external pump. After a 10 minute pre-incubation period the mucosal chamber is removed and flushed through with TC199-M media to remove any mucus build up, finally the luminal side is filled with 4 ml of TC199-M containing $^{14}C$-Mannitol (a non-electrolyte that is poorly absorbed by the gastrointestinal tract) at a concentration of $5\times10^5$ dpm/ml and returned to the glass chamber.

In order to measure the permeability of the isolated duodenal mucosa to mannitol, duplicate 150 μl aliquots of the serosal side solution are taken at 10, 20, 30, 60, 120, 180 and 240 minutes, following its addition to the mucosal side. The amount of mannitol absorbed is determined by liquid scintillation counting. As a positive control, paraquat (40 mg paraquat ion/ml), a known topical irritant to the gastrointestinal tract, is added to the mucosal chamber 30 minutes after the start of the incubation in order to demonstrate that the model is capable of detecting mucosal damage. The rodent control agents (fusion proteins or protein conjugates, see for example Examples 6 to 8 above) are added by direct addition of a small volume to the mucosal chamber at 30 minutes after the start of the incubation and the time course profile of mannitol absorption is monitored. This is compared with contemporary negative controls for both proximal and distal segments of rat duodenum run in parallel.

The methodology described above uses duodenal tissue, however, other areas of the gastrointestinal tract may be substituted and tested using the same procedure as described above.

Example 10

In Vivo Testing of Protein Conjugates and Fusion Proteins 10.1 Testing for Efficacy by Oral Gavage in Mouse Mice (18 in total, 9 per group) will be dosed orally by gavage with i) protein conjugate or fusion protein (see in particular Examples 6 to 8 above; group 1 mice), or ii) inert vehicle (e.g. polyethylene glycol; group 2 mice). Animals will be terminated 24, 48 and 72 hours post dosing, with clinical observations being made regularly throughout the study. Following termination, duodenal, jejunal, ileal and colonic tissue will be fixed in formal buffered saline, processed and embedded into wax and stained with H&E for pathological assessment.

Fusion proteins/protein conjugates are employed at the following test concentrations (given in mg of compound per kg bodyweight): 8 mg/kg, 5 mg/kg and 3 mg/kg.

The invention claimed is:

1. A rodent control agent comprising an antibody component that (i) contains 6 complementary determining region (CDR) sequences or (ii) is a heavy chain obtained from camels and sharks and contains 3 CDR sequences and lacks a light chain, wherein the antibody component binds to a rodent specific peptide epitope (RSPE), the RSPE consisting of an oligopeptide fragment of a protein that is expressed in a rodent selected from the group consisting of rats and mice, wherein the oligopeptide fragment sequence represents an extracellular continuous peptide epitope that has a percentage identity of 60% or less with a corresponding linear peptide sequence from a homologous protein from a non-target animal selected from the group consisting of humans and birds, and wherein the antibody component is linked to a toxic component.

2. A rodent control agent according to claim 1, wherein said rodent control agent comprises a fusion protein, said fusion protein comprising a first protein component and a second protein component, said first protein component being the antibody component and said second protein component being selected from the group consisting of a toxin, an immunogen and a hormone.

3. A rodent control agent according to claim 2, wherein said first and second protein components are linked to each other via a peptide linker.

4. A rodent control agent according to claim 3, wherein said peptide linker includes Glycine and Serine residues, the linker comprising at least three ($Gly_4Ser$) motifs.

5. A rodent control agent according to claim 1, wherein said rodent control agent comprises a protein conjugate, said protein conjugate comprising the antibody chemically conjugated to the toxic component.

6. A rodent control agent according to claim 1, wherein the toxic component is a protein toxin.

7. A rodent control agent according to claim 6, wherein said toxin is a) a full-length RNA glycosidase or b) a toxic domain of a RNA glycosidase.

8. A rodent control agent according to claim 7, wherein the toxin is gelonin.

9. A rodent control agent according to claim 1, wherein the protein that is expressed in the rodent is expressed in the gastro-intestinal epithelium of the rodent.

10. A rodent control agent according to claim 9, wherein the protein that is expressed in the gastro-intestinal epithelium is selected from the group consisting of Rat CATB(0+), Rat GCC, Rat PLB, Rat LPH, Mouse LPH, Rat AMPN, Rat MCDL, Rat SCAB, Rat KCV2, Rat PEP T1, Rat CD155, Rat GTR2, Rat CFTR, Rat CNT2, Rat MDR1, Mouse MDR1, Rat Sucrase-Isomaltase, Mouse GLUT7, Rat GTR5, Rat Npt2A, Rat OAT-B, Rat ASBT, Rat CAT1, Rat OATP3, Rat ABCG8, Rat GTR8, Rat MRP1, Rat CNT1, Rat UT-B, Rat DRA1, Mouse ENT1 and Rat ENT1.

11. A rodent control agent according to claim 10, wherein the RSPE is provided by an amino acid sequence selected from the group consisting of SEQ ID NOs: 27-36.

12. A rodent control agent according to claim 1, wherein the antibody component is a single-chain antibody which is a scFv.

13. A rodent control agent according to claim 12, wherein the single chain antibody is devoid of light chains and is derived from the Camelidae or from the Chondrichthyes.

14. A rodent control agent according to claim 1, wherein the antibody component exhibits displaceable binding to the RSPE, but does not exhibit displaceable binding to: i) a homologous protein from the non-target animal, or ii) a corresponding epitope from the homologous protein from the non-target animal.

15. A rodent control agent according to claim 1 in the form of a composition including at least one additive.

16. A rodent control agent according to claim 15 wherein said additive is a first generation anti-coagulant or a second generation anti-coagulant.

17. A rodent control agent according to claim 15, wherein at least one additive has the function of making the composition palatable to the rodent.

18. A rodent control agent according to claim 11, wherein the RSPE is provided by an amino acid sequence consisting of SEQ ID NO: 27.

* * * * *

SEQUENCE LISTING

```
<160> NUMBER OF SEQ ID NOS: 59

<210> SEQ ID NO 1
<211> LENGTH: 15
<212> TYPE: PRT
<213> ORGANISM: Artificial sequence
<220> FEATURE:
<223> OTHER INFORMATION: RSPE from Rat oligopeptide transporter PepT1

<400> SEQUENCE: 1

Val Ile Arg Ser Arg Ala Ser Asp Gly Cys Leu Glu Val Lys Glu
1               5                   10                  15


<210> SEQ ID NO 2
<211> LENGTH: 11
<212> TYPE: PRT
<213> ORGANISM: Artificial sequence
```

<220> FEATURE:
<223> OTHER INFORMATION: RSPE from Rat oligopeptide transporter PepT1

<400> SEQUENCE: 2

Cys Ser Ser Asp Phe Lys Ser Ser Asn Leu Asp
1               5                   10

<210> SEQ ID NO 3
<211> LENGTH: 17
<212> TYPE: PRT
<213> ORGANISM: Artificial sequence
<220> FEATURE:
<223> OTHER INFORMATION: RSPE from Rat CD155

<400> SEQUENCE: 3

Ser Asn Val Asn Gly Ser Tyr Arg Glu Met Lys Glu Thr Gly Ser Gln
1               5                   10                  15

Pro

<210> SEQ ID NO 4
<211> LENGTH: 15
<212> TYPE: PRT
<213> ORGANISM: Artificial sequence
<220> FEATURE:
<223> OTHER INFORMATION: RSPE from Rat GTR2

<400> SEQUENCE: 4

Gly Thr Asp Thr Pro Leu Ile Val Thr Pro Ala His Thr Thr Pro
1               5                   10                  15

<210> SEQ ID NO 5
<211> LENGTH: 16
<212> TYPE: PRT
<213> ORGANISM: Artificial sequence
<220> FEATURE:
<223> OTHER INFORMATION: RSPE from Rat CFTR chloride transporter

<400> SEQUENCE: 5

Leu Lys Asn Asn Pro Val Asn Gly Gly Asn Asn Gly Thr Lys Ile Ala
1               5                   10                  15

<210> SEQ ID NO 6
<211> LENGTH: 13
<212> TYPE: PRT
<213> ORGANISM: Artificial sequence
<220> FEATURE:
<223> OTHER INFORMATION: RSPE from Rat CNT2 nucleoside transporter

<400> SEQUENCE: 6

Trp Gln Asp Lys Glu Ser Ser Leu Arg Asn Leu Ala Lys
1               5                   10

<210> SEQ ID NO 7
<211> LENGTH: 12
<212> TYPE: PRT
<213> ORGANISM: Artificial sequence
<220> FEATURE:
<223> OTHER INFORMATION: RSPE from Rat CATB(O+) colonic aimino acid
      transporter

<400> SEQUENCE: 7

Gly Gly Asp Met Phe Met Asn Ile Ser Trp Val Asn
1               5                   10

<210> SEQ ID NO 8
<211> LENGTH: 15
<212> TYPE: PRT
<213> ORGANISM: Artificial sequence
<220> FEATURE:
<223> OTHER INFORMATION: RSPE from Rat MDR1

<400> SEQUENCE: 8

Ser Phe Thr Pro Ser Arg Asp Pro His Ser Asp Arg Ala Ile Thr
1 5 10 15

<210> SEQ ID NO 9
<211> LENGTH: 14
<212> TYPE: PRT
<213> ORGANISM: Artificial sequence
<220> FEATURE:
<223> OTHER INFORMATION: RSPE from Mouse MDR1

<400> SEQUENCE: 9

Ser Phe Thr Lys Ala Glu Ala Ser Ile Leu Pro Ser Ile Thr
1 5 10

<210> SEQ ID NO 10
<211> LENGTH: 17
<212> TYPE: PRT
<213> ORGANISM: Artificial sequence
<220> FEATURE:
<223> OTHER INFORMATION: RSPE from Rat sucrase-isomaltase

<400> SEQUENCE: 10

Tyr Asn Ala Glu Ser Ile Thr Asn Glu Asn Ala Gly Leu Lys Ala Thr
1 5 10 15

Leu

<210> SEQ ID NO 11
<211> LENGTH: 12
<212> TYPE: PRT
<213> ORGANISM: Artificial sequence
<220> FEATURE:
<223> OTHER INFORMATION: RSPE from Mouse GLUT7

<400> SEQUENCE: 11

Asn Thr Pro His Lys Val Leu Lys Ser Phe Tyr Asn
1 5 10

<210> SEQ ID NO 12
<211> LENGTH: 11
<212> TYPE: PRT
<213> ORGANISM: Artificial sequence
<220> FEATURE:
<223> OTHER INFORMATION: RSPE from Mouse GLUT7/Rat GTR5

<400> SEQUENCE: 12

Tyr Tyr Asp Arg Asn Lys Glu Asn Ile Glu Ser
1 5 10

<210> SEQ ID NO 13
<211> LENGTH: 15
<212> TYPE: PRT
<213> ORGANISM: Artificial sequence
<220> FEATURE:
<223> OTHER INFORMATION: RSPE from Rat Npt2a

<400> SEQUENCE: 13

Pro Glu Thr Lys Glu Ala Ser Thr Ser Met Ser Arg Val Glu Ala
1 5 10 15

```
<210> SEQ ID NO 14
<211> LENGTH: 23
<212> TYPE: PRT
<213> ORGANISM: Artificial sequence
<220> FEATURE:
<223> OTHER INFORMATION: RSPE from Rat OATP-B

<400> SEQUENCE: 14

Leu Gly Ala Gln Pro Gly Pro Ser Leu Phe Pro Gly Cys Ser Glu Pro
1               5                   10                  15

Cys Ser Cys Gln Ser Asp Asp
            20


<210> SEQ ID NO 15
<211> LENGTH: 17
<212> TYPE: PRT
<213> ORGANISM: Artificial sequence
<220> FEATURE:
<223> OTHER INFORMATION: RSPE from Rat OATP-B

<400> SEQUENCE: 15

Gln Pro Gly Pro Ser Leu Phe Pro Gly Cys Ser Glu Pro Cys Ser Cys
1               5                   10                  15

Gln


<210> SEQ ID NO 16
<211> LENGTH: 13
<212> TYPE: PRT
<213> ORGANISM: Artificial sequence
<220> FEATURE:
<223> OTHER INFORMATION: RSPE from Rat ASBT

<400> SEQUENCE: 16

Asp Ala Glu Phe Leu Glu Lys Thr Asp Asn Asp Met Asp
1               5                   10


<210> SEQ ID NO 17
<211> LENGTH: 12
<212> TYPE: PRT
<213> ORGANISM: Artificial sequence
<220> FEATURE:
<223> OTHER INFORMATION: RSPE from Rat CaT1

<400> SEQUENCE: 17

Gln Ala Phe Gln Gln Gln Asp Asp Leu Tyr Ser Glu
1               5                   10


<210> SEQ ID NO 18
<211> LENGTH: 16
<212> TYPE: PRT
<213> ORGANISM: Artificial sequence
<220> FEATURE:
<223> OTHER INFORMATION: RSPE from Rat OATP3

<400> SEQUENCE: 18

Ser Tyr Lys Gly Val Gln His Gln Leu His Val Glu Ser Lys Val Leu
1               5                   10                  15


<210> SEQ ID NO 19
<211> LENGTH: 14
<212> TYPE: PRT
<213> ORGANISM: Artificial sequence
<220> FEATURE:
<223> OTHER INFORMATION: RSPE from Rat ABCG8
```

-continued

<400> SEQUENCE: 19

Gln Ile Gln Phe Asn Gly His Ile Tyr Thr Thr Gln Ile Gly
1 5 10

<210> SEQ ID NO 20
<211> LENGTH: 18
<212> TYPE: PRT
<213> ORGANISM: Artificial sequence
<220> FEATURE:
<223> OTHER INFORMATION: RSPE from Rat GTR8

<400> SEQUENCE: 20

His Val Gly Leu Leu Val Pro Ile Ser Ala Glu Pro Ala Asp Val His
1 5 10 15

Leu Gly

<210> SEQ ID NO 21
<211> LENGTH: 14
<212> TYPE: PRT
<213> ORGANISM: Artificial sequence
<220> FEATURE:
<223> OTHER INFORMATION: RSPE from Rat MRP1

<400> SEQUENCE: 21

Met Phe Ala Gly Pro Glu Ile Leu Glu Leu Ile Ile Asn Phe
1 5 10

<210> SEQ ID NO 22
<211> LENGTH: 16
<212> TYPE: PRT
<213> ORGANISM: Artificial sequence
<220> FEATURE:
<223> OTHER INFORMATION: RSPE from Rat CNT1

<400> SEQUENCE: 22

His Ser His Ser Ser Leu Pro Glu Gly Glu Gly Gly Leu Asn Lys Ala
1 5 10 15

<210> SEQ ID NO 23
<211> LENGTH: 12
<212> TYPE: PRT
<213> ORGANISM: Artificial sequence
<220> FEATURE:
<223> OTHER INFORMATION: RSPE from Rat UT-B

<400> SEQUENCE: 23

Pro Ser Lys Leu Phe Met Pro Val Ser Ser Val Pro
1 5 10

<210> SEQ ID NO 24
<211> LENGTH: 18
<212> TYPE: PRT
<213> ORGANISM: Artificial sequence
<220> FEATURE:
<223> OTHER INFORMATION: RSPE from Rat DRA1

<400> SEQUENCE: 24

Leu Ser Ser Ser Ser Ala Glu Asn Asp Ser Met Ile Glu Glu Lys Val
1 5 10 15

Met Val

<210> SEQ ID NO 25
<211> LENGTH: 16
<212> TYPE: PRT
<213> ORGANISM: Artificial sequence
<220> FEATURE:
<223> OTHER INFORMATION: RSPE from Mouse ENT1

<400> SEQUENCE: 25

Lys Ala Arg His Cys Gly Ala Gln Arg His His Phe Val Phe Lys His
1 5 10 15

<210> SEQ ID NO 26
<211> LENGTH: 18
<212> TYPE: PRT
<213> ORGANISM: Artificial sequence
<220> FEATURE:
<223> OTHER INFORMATION: RSPE from Rat ENT1

<400> SEQUENCE: 26

Thr Asn Gln Ser Cys Glu Ser Thr Glu Ala Leu Ala Asp Pro Ser Val
1 5 10 15

Ser Leu

<210> SEQ ID NO 27
<211> LENGTH: 10
<212> TYPE: PRT
<213> ORGANISM: Artificial sequence
<220> FEATURE:
<223> OTHER INFORMATION: RSPE from Rat GCC

<400> SEQUENCE: 27

Val Ser Gly Arg Phe Pro Ser Glu Arg Ser
1 5 10

<210> SEQ ID NO 28
<211> LENGTH: 19
<212> TYPE: PRT
<213> ORGANISM: Artificial sequence
<220> FEATURE:
<223> OTHER INFORMATION: RSPE from Rat PLB

<400> SEQUENCE: 28

Ala Glu Asp Leu Trp Ile Gln Ala Lys Glu Leu Val Arg His Leu Lys
1 5 10 15

Asp Asn Pro

<210> SEQ ID NO 29
<211> LENGTH: 12
<212> TYPE: PRT
<213> ORGANISM: Artificial sequence
<220> FEATURE:
<223> OTHER INFORMATION: RSPE from Rat LPH

<400> SEQUENCE: 29

Glu Asp Ala Ala Pro Thr Ala Ser Pro Val Gln Ser
1 5 10

<210> SEQ ID NO 30
<211> LENGTH: 44
<212> TYPE: PRT
<213> ORGANISM: Artificial sequence
<220> FEATURE:
<223> OTHER INFORMATION: RSPE from Mouse LPH

<400> SEQUENCE: 30

Arg Tyr Val Gln Val Cys Ala Leu Cys Arg Phe Ser Thr Val Phe Ser
1 5 10 15

Pro Arg Leu Pro Glu Pro Val Lys Gly Glu Arg Arg Phe Ser His Ile
20 25 30

Ser Leu Asn Gln Asp Leu Pro Arg Pro Leu Phe Pro
35 40

<210> SEQ ID NO 31
<211> LENGTH: 13
<212> TYPE: PRT
<213> ORGANISM: Artificial sequence
<220> FEATURE:
<223> OTHER INFORMATION: RSPE from Rat AMPN

<400> SEQUENCE: 31

Gly Ser Thr Ser Ala Thr Thr Ser Thr Thr Asn Pro Ala
1 5 10

<210> SEQ ID NO 32
<211> LENGTH: 18
<212> TYPE: PRT
<213> ORGANISM: Artificial sequence
<220> FEATURE:
<223> OTHER INFORMATION: RSPE from Rat MCDL

<400> SEQUENCE: 32

Asn Lys Asp Ile Leu Leu Thr Thr Val Pro Met Glu Thr Glu Arg Thr
1 5 10 15

Ile Arg

<210> SEQ ID NO 33
<211> LENGTH: 15
<212> TYPE: PRT
<213> ORGANISM: Artificial sequence
<220> FEATURE:
<223> OTHER INFORMATION: RSPE from Rat SCAB

<400> SEQUENCE: 33

Leu Pro Gln Asp Leu Val Gly Met Gly Tyr Ala Pro Asp Arg Ile
1 5 10 15

<210> SEQ ID NO 34
<211> LENGTH: 9
<212> TYPE: PRT
<213> ORGANISM: Artificial sequence
<220> FEATURE:
<223> OTHER INFORMATION: RSPE from Rat SCAB

<400> SEQUENCE: 34

Ser Ser Asn Pro Ala Pro Gly Ser Thr
1 5

<210> SEQ ID NO 35
<211> LENGTH: 15
<212> TYPE: PRT
<213> ORGANISM: Artificial sequence
<220> FEATURE:
<223> OTHER INFORMATION: RSPE from Rat KCV2

<400> SEQUENCE: 35

Asp Gln Arg His Gly Lys Gly Ser Pro Arg Glu His Asp Leu Glu
1 5 10 15

-continued

<210> SEQ ID NO 36
<211> LENGTH: 15
<212> TYPE: PRT
<213> ORGANISM: Artificial sequence
<220> FEATURE:
<223> OTHER INFORMATION: RSPE from Rat CATB(O+) colonic amino acid transporter

<400> SEQUENCE: 36

Asp Thr Gly Gly Asp Met Phe Met Asn Ile Ser Trp Val Asn Ser
1 5 10 15

<210> SEQ ID NO 37
<211> LENGTH: 22
<212> TYPE: DNA
<213> ORGANISM: Artificial sequence
<220> FEATURE:
<223> OTHER INFORMATION: RoPro-9 primer

<400> SEQUENCE: 37
aggtscagct gcagsagtcw gg 22

<210> SEQ ID NO 38
<211> LENGTH: 38
<212> TYPE: DNA
<213> ORGANISM: Artificial sequence
<220> FEATURE:
<223> OTHER INFORMATION: RoPro-28 primer

<400> SEQUENCE: 38
ccaggggcca gtggatagac agatgggggt gtcgtttt 38

<210> SEQ ID NO 39
<211> LENGTH: 36
<212> TYPE: DNA
<213> ORGANISM: Artificial sequence
<220> FEATURE:
<223> OTHER INFORMATION: RoPro-6 Primer

<400> SEQUENCE: 39
gaggtgaagc tgcaggagtc aggacctagc ctggtg 36

<210> SEQ ID NO 40
<211> LENGTH: 32
<212> TYPE: DNA
<213> ORGANISM: Artificial sequence
<220> FEATURE:
<223> OTHER INFORMATION: RoPro-25 primer

<400> SEQUENCE: 40
tgaggagacg gtgaccgtgg tcccttggcc cc 32

<210> SEQ ID NO 41
<211> LENGTH: 32
<212> TYPE: DNA
<213> ORGANISM: Artificial sequence
<220> FEATURE:
<223> OTHER INFORMATION: RoPro-3 primer

<400> SEQUENCE: 41
ggtgatatcg tkctcacyca rtctccagca at 32

<210> SEQ ID NO 42
<211> LENGTH: 32
<212> TYPE: DNA
<213> ORGANISM: Artificial sequence
<220> FEATURE:
<223> OTHER INFORMATION: RoPro-4 primer

<400> SEQUENCE: 42
gggaagatgg atccagttgg tgcagcatca gc 32

<210> SEQ ID NO 43
<211> LENGTH: 34
<212> TYPE: DNA
<213> ORGANISM: Artificial sequence
<220> FEATURE:
<223> OTHER INFORMATION: scFv oligo 1 primer

<400> SEQUENCE: 43
agcccgccat ggccgatatc gttctcactc aatc 34

<210> SEQ ID NO 44
<211> LENGTH: 57
<212> TYPE: DNA
<213> ORGANISM: Artificial sequence
<220> FEATURE:
<223> OTHER INFORMATION: scFv oligo 2 primer

<400> SEQUENCE: 44
cgccagagcc accgccaccg ctaccgccac cgcccttgat ctccagtttg gtgcctc 57

<210> SEQ ID NO 45
<211> LENGTH: 56
<212> TYPE: DNA
<213> ORGANISM: Artificial sequence
<220> FEATURE:
<223> OTHER INFORMATION: scFv oligo 3 primer

<400> SEQUENCE: 45
agcggtggcg gtggctctgg cggtggcggt agcgaggtcc agctgcagga gtctgg 56

<210> SEQ ID NO 46
<211> LENGTH: 76
<212> TYPE: DNA
<213> ORGANISM: Artificial sequence
<220> FEATURE:
<223> OTHER INFORMATION: scFv oligo 4 primer

<400> SEQUENCE: 46
ctatgaattc agtggtggtg gtggtggtgc ttgtcgtcgt cgtccttgta gtctgaggag 60
actgtgagag tggtgc 76

<210> SEQ ID NO 47
<211> LENGTH: 36
<212> TYPE: DNA
<213> ORGANISM: Artificial sequence
<220> FEATURE:
<223> OTHER INFORMATION: scFv oligo 5 primer

<400> SEQUENCE: 47
agcccgccat ggccgaggtc cagctgcagg agtctg 36

<210> SEQ ID NO 48
<211> LENGTH: 58
<212> TYPE: DNA
<213> ORGANISM: Artificial sequence
<220> FEATURE:
<223> OTHER INFORMATION: scFv oligo 6 primer

<400> SEQUENCE: 48
cgccagaacc acctccgccg cttccgccac cgcctgagga gactgtgaga gtggtgcc 58

-continued

<210> SEQ ID NO 49
<211> LENGTH: 55
<212> TYPE: DNA
<213> ORGANISM: Artificial sequence
<220> FEATURE:
<223> OTHER INFORMATION: scFv oligo 7 primer

<400> SEQUENCE: 49
agcggcggag gtggttctgg cggtggcgga agcgatatcg ttctcactca atctc 55

<210> SEQ ID NO 50
<211> LENGTH: 76
<212> TYPE: DNA
<213> ORGANISM: Artificial sequence
<220> FEATURE:
<223> OTHER INFORMATION: scFv oligo 8 primer

<400> SEQUENCE: 50
gtatgaattc agtggtggtg gtggtggtgc ttgtcgtcgt cgtccttgta gtccttgatc 60
tccagtttgg tgcctc 76

<210> SEQ ID NO 51
<211> LENGTH: 49
<212> TYPE: DNA
<213> ORGANISM: Artificial sequence
<220> FEATURE:
<223> OTHER INFORMATION: RoPro070 petEK/rGrzB F1 primer

<400> SEQUENCE: 51
ggtaccgacg acgacgacaa gatcatcggt ggtcacgaag ctaagccac 49

<210> SEQ ID NO 52
<211> LENGTH: 20
<212> TYPE: DNA
<213> ORGANISM: Artificial sequence
<220> FEATURE:
<223> OTHER INFORMATION: RoPro067 rGrzB R primer

<400> SEQUENCE: 52
agctggcggc cgcctaggac 20

<210> SEQ ID NO 53
<211> LENGTH: 25
<212> TYPE: DNA
<213> ORGANISM: Artificial sequence
<220> FEATURE:
<223> OTHER INFORMATION: RoPro076 petEK/rGrzB F2 primer

<400> SEQUENCE: 53
agatctgggt accgacgacg acgac 25

<210> SEQ ID NO 54
<211> LENGTH: 21
<212> TYPE: DNA
<213> ORGANISM: Artificial sequence
<220> FEATURE:
<223> OTHER INFORMATION: pET F primer

<400> SEQUENCE: 54
tcggtgatgt cggcgatata g 21

<210> SEQ ID NO 55
<211> LENGTH: 44
<212> TYPE: DNA
<213> ORGANISM: Artificial sequence
<220> FEATURE:
<223> OTHER INFORMATION: RoPro 071 G4S/rGrzB R1 primer -continued

```
<400> SEQUENCE: 55

actacctccg ccaccggact tcttcatagt tttcttgatc cagg                        44


<210> SEQ ID NO 56
<211> LENGTH: 54
<212> TYPE: DNA
<213> ORGANISM: Artificial sequence
<220> FEATURE:
<223> OTHER INFORMATION: RoPro 074 rGrzB/G4S/VHVL F primer

<400> SEQUENCE: 56

gaagaagtcc ggtggcggag gtagtgaggt ccagctgcag gagtctggcc ctgg              54


<210> SEQ ID NO 57
<211> LENGTH: 55
<212> TYPE: DNA
<213> ORGANISM: Artificial sequence
<220> FEATURE:
<223> OTHER INFORMATION: RoPro 075 pET/VHVL R primer

<400> SEQUENCE: 57

tgctcgagtg cggccgctta ttacttgatc tccagtttgg tgcctccacc gaacg             55


<210> SEQ ID NO 58
<211> LENGTH: 55
<212> TYPE: DNA
<213> ORGANISM: Artificial sequence
<220> FEATURE:
<223> OTHER INFORMATION: RoPro 072 rGrzB/G4S/VLVH F primer

<400> SEQUENCE: 58

gaagaagtcc ggtggcggag gtagtgatat cgttctcact caatctccag caatc             55


<210> SEQ ID NO 59
<211> LENGTH: 53
<212> TYPE: DNA
<213> ORGANISM: Artificial sequence
<220> FEATURE:
<223> OTHER INFORMATION: RoPro 073 VLVH/pET R primer

<400> SEQUENCE: 59

tgctcgagtg cggccgctta ttatgaggag actgtgagag tggtgccttg gcc               53
```